(12) United States Patent
Rice et al.

(10) Patent No.: US 7,795,380 B2
(45) Date of Patent: Sep. 14, 2010

(54) COMPOSITIONS AND METHODS FOR NUCLEIC ACID DELIVERY

(75) Inventors: Kevin G. Rice, Iowa City, IA (US); Garrett R. Rettig, Iowa City, IA (US); Nicholas J. Baumhover, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 522 days.

(21) Appl. No.: 11/757,848

(22) Filed: Jun. 4, 2007

(65) Prior Publication Data
US 2008/0213898 A1 Sep. 4, 2008

Related U.S. Application Data

(60) Provisional application No. 60/810,278, filed on Jun. 2, 2006.

(51) Int. Cl.
*C07K 2/00* (2006.01)
(52) U.S. Cl. ...................................... 530/300
(58) Field of Classification Search ................ None
See application file for complete search history.

(56) References Cited

U.S. PATENT DOCUMENTS

| | | |
|---|---|---|
| 6,312,956 B1 | 11/2001 | Lane |
| 6,720,310 B1 | 4/2004 | Branden et al. |
| 2005/0170504 A1 | 8/2005 | Boehm et al. |

FOREIGN PATENT DOCUMENTS

| | | |
|---|---|---|
| WO | WO 99/49067 | 9/1999 |
| WO | WO 00/37659 | 6/2000 |

OTHER PUBLICATIONS

M. Smolarsky and D.E. Doshland. J. Biol. Chem. (1980) 255(15) pp. 7244-7249.*
Subbarao, et al., "pH-Dependent Bilayer Destabilization by an Amphipathic Peptide," Biochemistry (1987) 26(11): 2964-2972.
Boeckle, et al., "Melittin Analogs with High Lytic Activity at Endosomal pH Enhance Transfection with Purified Targeted PEI Polyplexes," Journal of Controlled Release 112 (2006) 240-248.
Cartier, et al., "Utilization of Synthetic Peptides Containing Nuclear Localization Signals for Nonviral Gene Transfer Systems," Gene Ther. Feb. 2002 9(3), p. 157-67.
Chan, et al., "Using Nuclear Targeting Signals to Enhance Non-Viral Gene Transfer," Immunol. Cell Biol. Apr. 2002 80(2), p. 119-30.
Ciolina, et al., "Coupling of Nuclear Localization Signals to Plasmid DNA and Specific Interaction of the Conjugates with Importin α," Bioconjugate Chem. 1999, 10, 49-55.
Collas, et al., "Rapid Targeting of Plasmid DNA to Zebrafish Embryo Nuclei by the Nuclear Localization Signal of SV40 T Antigen," Mol. Mar. Biol. Biotechnol. Mar. 1997, 6(1), p. 48-58.
Dang, et al.,"Identification of the Human c-*myc* Protein Nuclear Translocation Signal," Mol. Cell. Biol. (1988) 8(10): 4048-4054.
Derossi, et al., "The Third Helix of the Antennapedia Homeodomain Translocates through Biological Membranes," J. Biol. Chem. (1994) 269(14): 10444-10450.
Derossi, et al., "Trojan Peptides: the Penetratin System for Intracellular Delivery," Trends Cell Biol. (1998) 8(2): 84-87.
Deshayes, et al., "Cell-penetrating Peptides: Tools for Intracellular Delivery of Therapeutics," Cell. Mol. Life Sci. (2005) 62(16): 1839-1849.
Gottschalk, et al., "A Novel DNA-Peptide Complex for Efficient Gene Transfer and Expression in Mammalian Cells," Gene Ther. (1996) 3: 448-457.
Kichler, et al., "Influence of Membrane-Active Peptides on Lipospermine/DNA Complex Mediated Gene Transfer," Bioconjugate Chem. 1997, 8, 213-221.
Kiefer, et al., "Competition Between Nuclear Localization and Secretory Signals Determines the Subcellular Fate of a Single CUG-Initiated Form of FGF3," EMBO J. (1994) 13(17): 4126-4136.
Kleinschmidt, et al., "Identification of Domains Involved in Nuclear Uptake and Histone Binding of Protein N1 of *Xenopus laevis*," EMBO J. (1988) 7(6): 1605-1614.
Kodama, et al., "The features and Shortcomings for Gene Delivery of Current Non-Viral Carriers," Curr. Med. Chem. 2006, 13(18), 2155-61.
Lee, et al., "A New Gene Delivery Formulation of Polyethylenimine/DNA Complexes Coated with PEG Conjugated Fusogenic Peptide," Journal of Controlled Release 76 (2001) 183-192.
Li, et al., "GALA: A Designed Synthetic pH-Responsive Amphipathic Peptide with Applications in Drug and Gene Delivery," Adv Drug Deliv Rev (2004) 56:967-985.
Li, et al., "Gene Therapy Progress and Prospects: Non-Viral Gene Therapy by Systemic Delivery," Gene Ther. Sep. 2006, 13(18), p. 1313-9.
Ludtke, et al., "A Nuclear Localization Signal Can Enhance Both the Nuclear Transport and Expression of 1 kb DNA," J. Cell Sci. Jun. 1999, 112 (pt 12), p. 2033-41.
Mahato, et al., "Peptide-Based Gene Delivery", Curr Opin Mol Ther (1999) 1(2): 226-243.
Martin, et al., "Peptide-Guided Gene Delivery," The AAPS Journal 2007; 9(1) E18-E29.
Midoux, et al., "Membrane Permeabilization and Efficient Gene Transfer by a Peptide Containing Several Histidines," Bioconjugate Chem. (1998) 9: 260-267.
Parente, et al., "Association of a pH-Sensitive Peptide with Membrane Vesicles: Role of Amino Acid Sequence," Biochemistry (1990) 29(37):8713-8719.

(Continued)

*Primary Examiner*—Andrew D Kosar
(74) *Attorney, Agent, or Firm*—Foley & Lardner LLP

(57) ABSTRACT

Compositions and methods are described for non-viral nucleic acid delivery. A targeting peptide capable of mediating targeting to a cell or subcellular compartment is derivatized with a photoaffinity label. Following an ionic interaction with a polynucleotide, such as DNA, and photolysis, the bioactive peptide becomes covalently attached to the DNA. Upon contact with a cell, the peptide facilities uptake of the peptide-polynucleotide conjugate into the cell or subcellular compartment. Methods for using this system for delivery of structural genes, including reporter genes, and detection of expression using bioluminescence are also described.

15 Claims, 8 Drawing Sheets

OTHER PUBLICATIONS

Parente, et al., "Mechanism of Leakage of Phospholipid Vesicle Contents Induced by the Peptide GALA," Biochemistry (1990) 29(37): 8720-8728.

Plank, et al., "The Influence of Endosome-Disruptive Peptides on Gene Transfer Using Synthetic Virus-Like Gene Transfer Systems," J. Biol. Chem. (1994) 269: 12918-12924.

Pooga, et al., "Cell Penetration by Transportan," FASEB J (1998) 12: 67-77.

Pooga, et al., "Cellular Translocation of Proteins by Transportan," FASEB J. (2001) 15(8): 1451-1453.

Rittner, et al., "New Basic Membrane-Destabilizing Peptides for Plasmid-Based Gene Delivery in Vitro and in Vivo," Molecular Therapy (2002) 5(2): 104-114.

Robbins, et al., "Two Interdependent Basic Domains in Nucleoplasmin Nuclear Targeting Sequence: Identification of a Class of Bipartite Nuclear Targeting Sequence," Cell (1991) 64(3): 615-623.

Schnapp, et al., "Exploratory Photochemistry of Fluorinated Aryl Azides. Implications for Design of Photoaffinity Labeling Reagents," Bioconjugate Chemistry (1993) 4: 172-177.

Schreiber, et al., "The Human Poly(ADP-Ribose) Polymerase Nuclear Localization Signal Is a Bipartite Element Functionally Separate from DNA Binding and Catalytic Activity," EMBO J. (1992) 11(9): 3263-3269.

Schuster, et al., "Multicomponent DNA Carrier with a Vesicular Stomatitis Virus G-Peptide Greatly Enhances Liver-Targeted Gene Expression in Mice," Bioconjug. Chem. (1999) 10:1075-1083.

Wagner, et al., "Influenza Virus Hemagglutinin HA-2 N-Terminal Fusogenic Peptides Augment Gene Transfer by Transferrin-Polylysine-DNA Complexes: Toward A Synthetic Virus-Like Gene-Transfer Vehicle," Proc. Natl. Acad. Sci. USA (1992) 89: 7934-7938.

Wagner, Ernst, "Application of Membrane-Active Peptides for Nonviral Gene Delivery," Advanced Drug Delivery Reviews 38 (1999) 279-289.

Wyman, et al., "Design, Synthesis, and Characterization of a Cationic Peptide That Binds to Nucleic Acids and Permeabilizes Bilayers," Biochemistry (1997) 36(10): 3008-3017.

* cited by examiner

Photolabeling Efficiency of PL-NLS-Y-$^{125}$I

*In Vivo* Transfection via Hydrodynamic Dose with 0.1 μg of PL Melittin Labeled pGl3

COMPOSITIONS AND METHODS FOR NUCLEIC ACID DELIVERY

CROSS-REFERENCE TO RELATED APPLICATIONS

This application claims priority to U.S. provisional patent application No. 60/810,278, filed Jun. 2, 2006, the entire disclosure of which is incorporated herein by reference.

GOVERNMENT SUPPORT

This invention was made with government support under Contract No. DK 063196 awarded by NIH. The government has certain rights in the invention.

FIELD OF THE INVENTION

The invention relates generally to nonviral nucleic acid delivery systems. More specifically, the invention relates to compounds and polynucleotide constructs comprising a targeting peptide covalently attached to a polynucleotide using a photolabeling moiety. The invention also relates to methods of making and using the polynucleotide construct to deliver nucleic acids to cells in vitro and in vivo.

BACKGROUND OF THE INVENTION

The delivery of nucleic acids to cells, particularly but not exclusively, in gene therapy, has many applications in the medical and scientific fields. For example, gene therapy may be used to introduce replacement genes, thereby correcting genetic defects, or to introduce therapeutic genes to specific cells. Delivery of nucleic acids that mediate RNA interference is another way to influence gene expression and treat disease.

Numerous techniques have been developed to introduce DNA into cells. Functional exogenous genes can be introduced to mammalian cells in vitro by a variety of physical methods, including transfection, direct microinjection, electroporation, and coprecipitation with calcium phosphate. Most of these techniques, however, are impractical for delivering genes to cells within intact animals. Therefore, viruses are typically used as carriers for a transgene. However, using viruses as carriers is not desirable since problems of immunogenicity, cytotoxicity, and insertional mutagenesis are associated with viral vectors. Consequently, efficient nonviral nucleic acid delivery systems are needed.

BRIEF SUMMARY OF THE INVENTION

The present invention generally relates to compounds and methods for non-viral nucleic acid delivery to cells and subcellular compartments. In one aspect, the invention provides a targeting peptide with a photolabel at the N- or C-terminus of the peptide. This compound can form an ionic interaction with a polynucleotide and, following photolysis, becomes covalently attached to the polynucleotide. The attachment of the present compounds to a polynucleotide enhances the efficient delivery of the polynucleotide to a particular cell type or a particular subcellular location.

In some embodiments, the compound comprises the following structure:

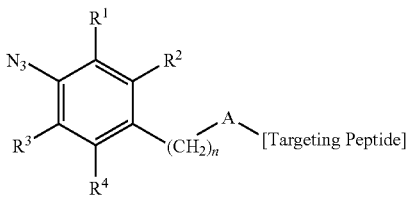

where $R^1$, $R^2$, $R^3$, and $R^4$ are independently selected from H, F, or Cl; n is an integer from 0 to 6; and A is CO or NH. The targeting peptide typically has an N-terminus and a C-terminus, and when A is CO, A forms an amide bond with an α-amino group of the N-terminal amino acid residue of the targeting peptide, and when A is NH, A forms an amide bond with the α-carboxyl group of the C-terminal amino acid residue of the targeting peptide. In some embodiments, A may form an amide bond with an amino acid side chain of the targeting peptide wherein the side chain is an amine or a carboxylic acid (e.g. lysine, aspartic acid, or glutamic acid). In some embodiments, $R^1$, $R^2$, $R^3$, and $R^4$ are F, and n is 1.

The targeting peptide can translocate and localize to the cytosol or a subcellular compartment of a cell, and may be selected from the following non-limiting classes of peptides: NLS peptides, fusogenic peptides, receptor ligands, antimicrobial peptides, and peptide hormones. The targeting peptide may be about 5 to about 50 amino acid residues long and is typically about 10 to about 30 amino acid residues long.

The targeting peptides of the compounds may comprise fragments or variants having at least 85%, at least 90%, or at least 95% amino acid sequence identity to a wild-type or native peptide. Where the targeting peptide comprises an NLS, the NLS may be a fragment a protein selected from the group consisting of SV40 large T NLS, M9 NLS, c-myc NLS, nucleoplasmin NLS, Xenopus N1 NLS, FGF3 NLS, and PARP NLS, or a variant having at least 95% amino acid sequence identity to the fragment. Exemplary NLS targeting peptides include those having at least 95% amino acid sequence identity to SEQ ID NOS: 16-25. Where the targeting peptide comprises a fusogenic peptide, the fusogenic peptide may be a fragment of a protein selected from the group consisting of melittin, HA-2, H5WYG, GAL4, KALA, JST-1, ppTG-1, VSV, penetratin, and transportan, or a variant having at least 95% amino acid sequence identity to the fragment. Exemplary fusogenic targeting peptides include those having at least 95% amino acid sequence identity to SEQ ID NOS: 26-36. Where the targeting peptide comprises a receptor ligand, exemplary receptor ligand peptides include those having at least 95% amino acid sequence identity to SEQ ID NOS: 37-58. Where the targeting peptide comprises an antimicrobial peptide, the antimicrobial peptide may be a fragment of a protein selected from the group consisting of: Abaecin, Apidaecins, Bac-5, Bac-7, Drosocin, Phosphenin, α-Defensins, β-Defensins, Insect defensins, Plant defensins, Protegrins, Drosomycin, Amphiphilic α-helical structure: Magainins, Dermaseptins, Bombinin, Cecropin, Esculentins-1, and Esculentins-2, or a variant having at least 95% amino acid sequence identity to the fragment. Exemplary antimicrobial peptides include those having at least 95% amino acid sequence identity to SEQ ID NOS: 84-98. Where the targeting peptide is a peptide hormone, exemplary peptide hormones include those having at least 95% amino acid sequence identity to SEQ ID NOS: 59-83. In some embodiments, where the targeting peptide is 20 amino acid residues or less, the variant of the targeting peptide has one, two or three amino acid substitutions. The substitutions may be conservative or nonconservative substitutions.

In some embodiments, the targeting peptide may further comprise a linker sequence. Typically the linker sequence comprises 1 to 10 amino acid residues. For example, the linker sequence comprises cationic amino acid residues and may be selected from SEQ ID NO: 99 or 100.

In a second aspect, the present invention provides constructs comprising polynucleotides photolabeled with the targeting peptide. The association of the targeting peptide with the polynucleotide, such as DNA, assists in targeting the polynucleotide to the cytosol or subcellular compartment of a cell. Thus, where the targeting peptide is an NLS, the invention provides a method of using the targeting polynucleotide conjugate compound to deliver DNA to the nuclei of cells in vivo. An advantage of the present system and methods is the ability to increase gene expression by a simple addition of a peptide to, e.g., plasmid DNA.

In some embodiments, the polynucleotide may be selected from DNA or RNA. The polynucleotide may encode a structural gene for gene therapy or be capable of mediating RNA interference. For example, a polynucleotide capable of mediating RNA interference may include short interfering nucleic acids (siNAs). In suitable embodiments, 1 to 3 molecules of the photolabeling compound comprising the targeting peptide are attached to the polynucleotide.

In a third aspect, the present invention provides methods of photoflashing a mixture of a polynucleotide and the photolabeling compound comprising a targeting peptide under conditions suitable to avoid UV self-crosslinking of the polynucleotide, whereby the polynucleotide is covalently linked to the targeting peptide through the photoaffinity label. Generally, the concentration of the compound is sufficient to provide a construct having 1 to 3 molecules of the compound attached to the polynucleotide. In suitable embodiments, the mixture comprises about 0.1 to about 10 pmol of the compound per µg of the polynucleotide.

The photolabeling attachment can be conducted on large scale and can be used to modify any polynucleotide. The association of the targeting peptide with the polynucleotide, such as DNA, assists in targeting the polynucleotide to the cytosol or subcellular compartment of a cell. Thus, where the targeting peptide is an NLS, the invention provides a method of using the targeting polynucleotide conjugate compound to deliver DNA to the nuclei of cells in vivo. An advantage of the present system and methods is the ability to increase gene expression by a simple addition of a peptide to, e.g., plasmid DNA. In further embodiments, the targeting peptide-polynucleotide conjugate comprises a reporter gene, such as luciferase, for the expression in mammalian cells. The reporter gene can be detected using bioluminescent imaging.

DETAILED DESCRIPTION OF THE INVENTION

Figure 1:
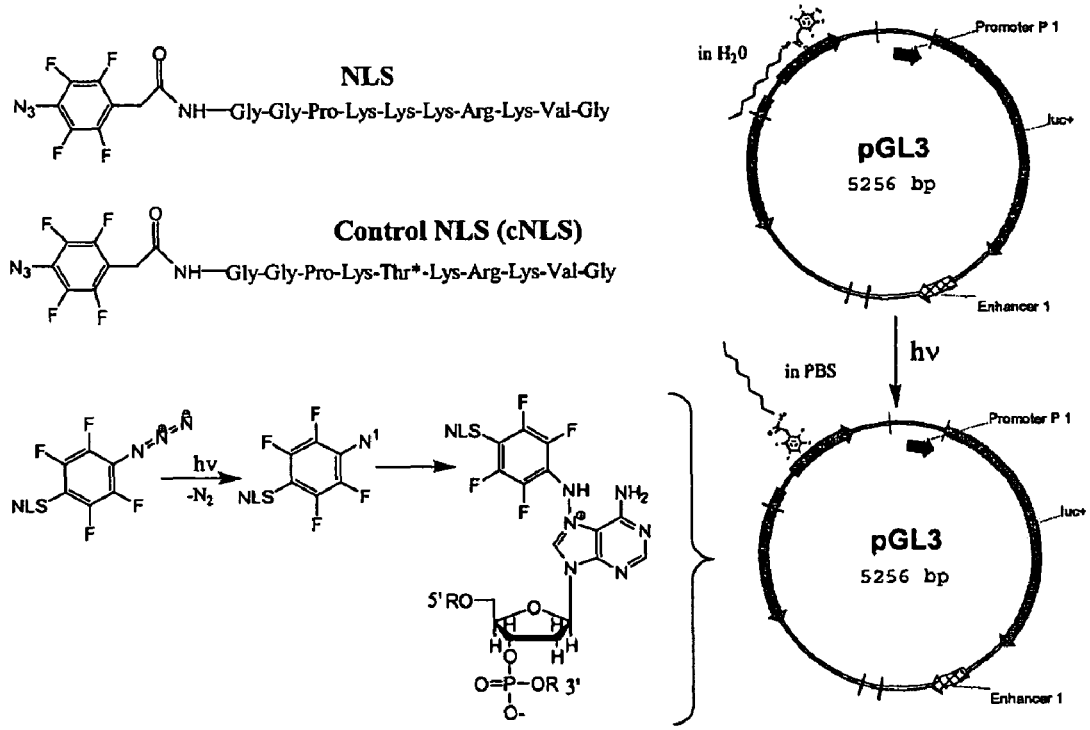
FIG. 1 is a schematic representation of the photoaffinity labeling reaction between the NLS substrate and DNA, represented by the plasmid, pGL3 (SEO ID NOS108 & 69 are disclosed respectively in order of appearance).

Disclosed herein are compounds and methods for delivering nucleic acids to cells. In particular, the compounds comprise a photolabel conjugated to a targeting peptide capable of translocating and localizing to the cytosol or a subcellular compartment of a cell. This compound can form an ionic interaction with a nucleic acid and, following photolysis, becomes covalently attached to the nucleic acid. The present inventors have discovered that nucleic acids photolabeled with a targeting peptide are useful in facilitating uptake or delivery of the nucleic acid to a specific cell or subcellular compartment.

All publications, patent applications, issued patents, and other documents referred to in the present disclosure are herein incorporated by reference as if each individual publication, patent application, issued patent, or other document were specifically and individually indicated to be incorporated by reference in its entirety. Definitions that are contained in text incorporated by reference are excluded to the extent that they contradict definitions in this disclosure.

DEFINITIONS

In the description that follows, a number of terms are utilized extensively. Definitions are herein provided to facilitate understanding of the invention. The terms defined below are more fully defined by reference to the specification as a whole.

Units, prefixes, and symbols may be denoted in their accepted SI form. Unless otherwise indicated, nucleic acids are written left to right in 5' to 3' orientation; amino acid sequences are written left to right in amino to carboxy orientation. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes.

The terms "a" and "an" as used herein mean "one or more" unless the singular is expressly specified.

The term "administering" includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically.

The term "fragment" in the context of a polypeptide is a stretch of amino acid residues of at least about 5 amino acids, at least about 7 amino acids, at least about 9 amino acids, or at least about 13 or more amino acids. The peptide typically is less than about 50 amino acids, or less than 30 amino acids. In many embodiments, the peptide is from about five to about 35 amino acids. To be active, any polypeptide must have sufficient length to display biological and/or immunological activity. The term "biological activity" refers to the capability of the natural, recombinant or synthetic peptide, or any peptide fragment thereof, to induce a specific response in appropriate animals or cells (e.g. receptor or ligand binding, membrane fusion, and/or translocation to the cytosol or a specific subcellular compartment).

The term "introduce" as applied to nucleic acids refers to incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). The term includes such nucleic acid introduction means as transfection, transformation, and transduction. The term also includes use of a targeting peptide/polynucleotide conjugate compound to deliver DNA to specific cells or subcellular compartments.

A "nuclear localization sequence (NLS)" refers to a polypeptide that is capable of directing localization of a protein or polynucleotide to the nucleus of a cell. In the context of nucleic acids, a NLS refers to a polynucleotide encoding such a NLS polypeptide. A "nuclear localization peptide (NLP)" is a polypeptide that comprises an NLS.

The terms "polynucleotide" or "nucleic acid" refer to a deoxyribopolynucleotide, ribopolynucleotide, or chimeras or analogues thereof that have the essential nature of a natural deoxy- or ribonucleotide in that they hybridize, under stringent hybridization conditions, to substantially the same nucleotide sequence as naturally occurring nucleotides and/or allow translation into the same amino acid(s) as the naturally occurring nucleotide(s). Unless otherwise indicated, the term includes reference to the specified sequence as well as the complementary sequence thereof. DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide," "peptide," and "protein" are used interchangeably to refer to a polymer of amino acid residues. The terms apply to amino acid polymers in which one or more amino acid residues is an artificial chemical analog of a corresponding naturally occurring amino acid, as well as to naturally occurring amino acid polymers. The terms polypeptide, peptide, and protein are also inclusive of modifications including, but not limited to, glycosylation, lipid attachment, sulfation, carboxylation, hydroxylation, ADP-ribosylation, and addition of other complex polysaccharides. To be active, any polypeptide must have sufficient length to display biological and/or immunological activity.

The terms "residue" or "amino acid residue" or "amino acid" are used interchangeably to refer to an amino acid that is incorporated into a protein, polypeptide, or peptide. The amino acid may be a naturally occurring amino acid and, unless otherwise limited, may encompass non-natural analogues of natural amino acids that can function in a similar manner as naturally occurring amino acids.

As used herein, the term "RNA interference" (RNAi) refers to the process of sequence-specific post-transcriptional gene silencing mediated by short interfering nucleic acids (siRNAs). The term "agent capable of mediating RNA interference" refers to siRNAs as well as DNA and RNA vectors that encode siRNAs when transcribed within a cell. As used herein, the term "siNA" refers to short interfering nucleic acid. The term is meant to encompass any nucleic acid molecules that are capable of mediating sequence specific RNA interference, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others.

A "spacer" refers to a sequence of amino acid residues that separates the two domains of amino acids comprising a bipartite NLS. Generally, a spacer comprises a length of about 10 to about 12 residues and may comprise any amino acid sequence because a particular sequence is typically not required for a bipartite NLS to show nuclear localization activity.

A "subcellular compartment" is a membrane-enclosed space within a cell. A cell is surrounded by a plasma membrane. Structurally, a cell is composed of membranes and the spaces enclosed by those membranes. The intracellular space is thus divided into a number of subcellular compartments. Examples of subcellular compartments include, but are not limited to, the nucleus, vacuole, mitochondria, lysosome, endoplasmic reticulum, Golgi, endosome, and chloroplast.

A "targeting peptide" is a polypeptide that is capable of mediating, either by itself or in conjunction with other cellular proteins, translocation across one or more cellular membranes to localize in a desired target site, which may be the cytosol or a subcellular compartment of a cell. The targeting peptide may be specific to a particular subcellular compartment. The targeting peptide may also be specific to cells of a particular tissue type. The targeting protein may be attached to one or more other compounds such as a polynucleotide, wherein the targeting peptide and attached compounds are delivered to the target site in vivo.

A "therapeutically effective amount" of a compound refers to an amount of the compound that alleviates, in whole or in part, symptoms associated with a disorder or disease, or slows or halts further progression or worsening of those symptoms, or prevents or provides prophylaxis for the disease or disorder in a subject at risk for developing the disease or disorder.

The terms "translocation" or "translocate" refer to the biological activity of a targeting peptide wherein the peptide mediates its own trafficking across a membrane. The translocation of the targeting peptide may be accomplished through the action of one or more native cellular proteins, which bind to the peptide and then traffic the peptide across a membrane. The targeting peptide may also translocate itself by making the membrane permeable to the peptide specifically or to the entire contents of subcellular compartment generally. For example, some targeting peptides may pass through a membrane following insertion into the lipid bilayer. The targeting peptide may also disrupt the membrane's integrity, thereby releasing all of the contents of a subcellular compartment into the cytosol.

The ability of a targeting peptide to translocate and localize to the cytosol or subcellular compartment is measured relative to a control peptide. Those of ordinary skill in the art are well able to design appropriate controls. For example, a control peptide may be a peptide having the same amino acid composition as the targeting peptide, but the sequence is rearranged in random or scrambled order. At least 5%, at least 10%, at least 25%, or at least 50% more molecules of a bona fide targeting peptide will translocate and localize to the desired target site compared to the control peptide.

A "variant" or "derivative" of a polypeptide can differ from a naturally occurring polypeptide in amino acid sequence or in ways that do not involve amino acid sequence modifications, or both. Non-sequence modifications include, but are not limited to, changes in acetylation, methylation, phosphorylation, carboxylation, or glycosylation. Variants may also include sequences that differ from the wild-type sequence by one or more conservative or non-conservative amino acid substitutions, deletions, or insertions which do not substantially diminish the biological activity of the polypeptide. Conservatively modified variants typically provide similar biological activity as the unmodified polypeptide sequence from which the conservatively modified variant was derived. Conservative substitutions typically include the substitution of one amino acid for another with similar characteristics. Conservative substitution tables providing functionally similar amino acids are well known in the art. For example, the following six groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic (Cationic): Arginine (R), Lysine (K), Histidine (H); Acidic (Anionic): Aspartic acid (D), Glutamic acid (E); Amide: Asparagine (N), Glutamine (Q). Biologically-active variants typically have at least 80%, at least 85%, at least 90%, at least 95%, or at least 99% amino acid sequence identity to the unmodified polypeptide.

The present invention provides compounds and methods to deliver nucleic acids to cells or tissues, as well as methods of making and using the compounds. Thus, in accordance with one aspect of the invention, there is provided a compound that once attached to a polynucleotide, can traffic the polynucleotide into the cell or direct its localization to a particular subcellular compartment. The compound includes a targeting peptide having an N-terminal amino acid residue, a C-terminal amino acid residue, and a photolabel covalently linked to either the N-terminal or C-terminal amino acid residue of the targeting peptide. The label is capable of covalent attachment to a polynucleotide under suitable conditions, e.g., upon photolysis. Any suitable peptide sequence capable of directing translocation and localization to the cytosol or subcellular compartment may be used in the present invention.

The photoaffinity label in the compounds of the invention can be an azide such as an azido salicylate, aryl azide (e.g. azido anilines and benzoates, ethidium monoazides, azido fluorenes, and the like) or a diazo compound (e.g., dizaopyrrolines). In some embodiments, compounds of the invention have the structure of Formula I:

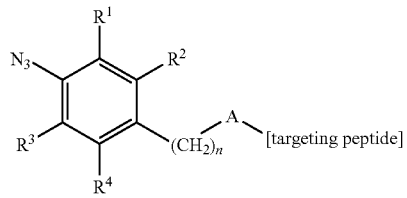

where $R^1$, $R^2$, $R^3$, and $R^4$ are independently selected from H, F, or Cl;

n is an integer from 0 to 6;

A is CO or NH;

wherein the targeting peptide is a peptide that can translocate and localize to the cytosol or a subcellular compartment of a cell; and wherein the targeting peptide is selected from the group consisting of NLS peptides, fusogenic peptides, receptor ligands, antimicrobial peptides, and peptide hormones.

In certain embodiments, the targeting peptide has an N-terminus and a C-terminus, and when A is CO, A forms an amide bond with an amino group of the N-terminal amino acid residue of the targeting peptide, and when A is NH, A forms an amide bond with the α-carboxyl group of the C-terminal amino acid residue of the targeting peptide. In certain embodiments of compounds of Formula I, $R^1 R^2$, $R^3$, and $R^4$ are all F. In some embodiments A is CO, and n is 0. In others, A is NH and n is 0. The photolabel, may be added to the peptide during the last step of solid phase synthesis and is attached to the N-terminus of the targeting peptide. The label is designed to photolyse and reacts preferentially with nucleophiles such as N7 on guanine. Schnapp et al., *Bioconjugate Chemistry* (1993) 4: 172-177.

It has been discovered by the present inventors that compounds comprising a short non-peptidic linker having from 1 to about 7 backbone atoms and/or lacking bulky fluorescent moieties (e.g., rhodamine) are effective in delivering nucleic acids to cells or subcellular compartments. In contrast, compounds that possess longer non-peptidic linkages between the aromatic ring and the attachment site of the targeting peptide and/or contain large fluorophores such as rhodamine may not be as effective in delivering nucleic acids to cells or subcellular compartments. In some embodiments, the non-peptidic linker backbone has fewer than about 7 atoms, fewer than about 6 atoms, fewer than about 5 atoms, fewer than about 4 atoms, or fewer than about 3 atoms.

In some embodiments, the targeting peptide may be conjugated to a photolabel at either the N- or C-terminus. For some targeting peptides, labeling at one of the N- or C-terminus may provide increased transfer efficiency in a variety of cell lines over peptides labeled at the other end. While not wishing to be bound by theory, changing the orientation may alter the membrane lytic activity of the peptide at different pH's. Thus, photolabel compounds are provided that may be conjugated at either the N- or C-terminus. Based on the disclosure herein, it is within the ordinary skill in the art to determine which orientation is the most efficient for the targeting peptides using routine experimentation.

The targeting peptides may comprise any amino acid sequence which mediates the translocation of that sequence across one or more cell or subcellular membranes thereby localizing the peptide to the cytosol or a subcellular compartment of the cell. Classes of peptides which have the translocating activity described herein include, but are not limited, nuclear localization sequences, fusogenic peptides, receptor ligands, antimicrobial peptides, and peptide hormones. In suitable embodiments, the compounds are linked through the photolabeling moiety to a polynucleotide. Consequently, when the polynucleotide-peptide construct is contacted with a cell, the targeting peptide directs the localization of the construct to a particular region of the cell, e.g. the cytosol of subcellular compartment.

The targeting peptides may also include fragments and variants of the peptides that are described herein. These derivative sequences may differ from the wild-type sequence by one or more conservative amino acid substitutions or by one or more non-conservative amino acid substitutions, deletions, or insertions which do not substantially diminish the biological activity of the peptide.

Nuclear Localization Sequences

In one embodiment, the targeting peptide comprises a nuclear localizing sequence (NLS) peptide having an N-terminal amino acid residue, a C-terminal amino acid residue and a photolabel covalently linked to either the N-terminal or C-terminal amino acid residue of the NLS peptide. Any suitable peptide sequence capable of directing localization to the nucleus may be used with the present invention.

For example, the NLSes shown in Table 1 or fragments or conservative variants thereof may comprise targeting peptides that may be used with the invention. It is not intended that the invention be limited to these sequences, as alternative embodiments may use any nuclear localization sequences within the spirit and scope of the invention.

TABLE 1

Nuclear Localization Sequences

| Protein | SEQ ID NO | Sequence |
|---|---|---|
| SV40 T | SEQ ID NO: 1 | PKKKRKV |
| Dorsal | SEQ ID NO: 2 | RRKRQR |
| RB | SEQ ID NO: 3 | KR-[11 aa spacer]-KKLR |
| N1N2 | SEQ ID NO: 4 | RKKRK-[12 aa spacer]-KKSK |
| Mat-α2 | SEQ ID NO: 5 | MNKIPIKDLLNPQ |
| PTHrP | SEQ ID NO: 6 | YLTQETNKVETYKEQPLKTPGKKKKG KP |
| hnRNP | SEQ ID NO: 7 | NQSSNFGPMKGGNFGGRSSGPYGGGG QYFAKPRNQGGY |
| Pho4 | SEQ ID NO: 8 | SANKVTKNKSNSSPYLNKRKGKPGPD S |
| rpL23a | SEQ ID NO: 9 | VHSHKKKKIRTSPTFTTPKTLRLRRQ PKYPRKSAPRRNKLDHY |
| rpL25 | SEQ ID NO: 10 | NAPSAKATAAKKAVVKGTNGKKALKV RTSATFRLPKTLKLAR |

In addition to the classic NLS sequence (SV40 large T antigen monopartite sequence, SEQ ID NO: 1), other monopartite and bipartite NLS sequences may be used to target either DNA or proteins to the nucleus. Each of the following NLS peptides may be synthesized with either a C- or N-terminal azido phenylalanine (PL), as described above.

Monopartite NLS sequence include those from M9 and c-myc. M9 is a non-classic 38 amino acid monopartite NLS derived from nuclear ribonucleoprotein (hnRNP) A1, that was used by Subramanian and coworkers to increase nuclear import of plasmid DNA. Subramanian et al., *Nat. Biotechnol.* (1999) 17(9):873-877. Human c-myc is a short-lived phosphoprotein found in the nucleus that is 439 amino acids in length. A peptide fragment Ml from residues 320 to 328 has the sequence PAAKRVKLD [SEQ ID NO: 11] that serves as the NLS. Dang and Lee. *Mol. Cell. Biol.* (1988) 8(10): 4048-4054.

Bipartite NLS sequences contain two essential domains of basic amino acids separated by a spacer that is generally 10 to 12 amino acids in length. Mahato et al., *Curr Opin Mol Ther* (1999) 1(2): 226-243. One of the most well known characterized bipartite NLSes is the Xenopus protein nucleoplasmin, which has two clusters of basic amino acids separated by a 10 residue spacer sequence. Nucleoplasmin has the sequence KRPAATKK-AGQAKKKK [SEQ ID NO: 12], which partially resembles the SV40 T antigen NLS with the lysine stretch at its carboxyl terminus. Robbins et al., *Cell* (1991) 64(3): 615-623.

Xenopus also contains a bipartite NLS derived from the N1 protein. Kleinschmidt et al. showed that the 24 amino acid sequence of the N1 NLS can be divided into two required nuclear uptake sequences of VRKKRKT (SEQ ID NO: 104) and AKKSKQE (SEQ ID NO: 105) joined by a 10 amino acid spacer to give the overall peptide VRKKRKTEEESPLKD-KDAKKSKQE [SEQ ID NO:13]. The amino acid sequence of the spacer region may be varied without loss of activity, since it has been shown that a lysine to threonine mutation of the spacer region does not influence nuclear accumulation. Kleinschmidt et al., *EMBO J.* (1988) 7(6): 1605-1614.

The mouse fibroblast growth factor 3 (FGF3) protein contains a bipartite NLS motif Kiefer and coworkers narrowed down the location of the NLS sequence from five possible regions in the protein sequence to the arginine rich site located in the N-terminal half of the protein. The two basic regions of the peptide are designated NLS1 with the sequence RLRR (SEQ ID NO: 106) and NLS2 made up by the amino acids RRRK (SEQ ID NO: 107). The two cationic clusters are joined by a 16 amino acid spacer giving the entire NLS sequence of RLRRDAGGRGGVYEHLGGAPRRRK [SEQ ID NO:14]. Point mutations in either or both of the NLS regions resulted in decreased or abolished nuclear accumulation, respectively. Kiefer et al., *EMBO J.* (1994) 13(17): 4126-4136.

Poly (ADP-ribose) polymerase (PARP) is a protein involved in DNA repair that contains a classical bipartite NLS sequence as well. Schreiber et al. have defined the NLS sequence as corresponding to residues 207 through 226 of the PARP protein with the sequence KRKGDEVDGVDE-CAKKSKK [SEQ ID NO: 15]. As with all other bipartite peptides, the two basic stretches are crucial for activity but not able to mediate nuclear uptake on their own. Experiments show that the 11 amino acid spacing between the basic clusters can be varied in length without affecting activity as long as K222 remains in the correct position. Schreiber et al., *EMBO J.* (1992) 11(9): 3263-3269.

NLS sequences such as those set forth in Table 1 or fragments or variants thereof may be used in the compounds of the invention. Any of the NLS targeting peptides described herein may be conjugated at its N- or C-terminus to a photolabel. In some embodiments, the targeting peptides may comprise one or more NLS sequences, and optionally, a linker sequence of about 1 to about 10 amino acids between the NLS and the photolabel (described in further detail below). Representative targeting peptides comprising an NLS, and a two amino acid linker sequences (GG or KK) at their N-termini are shown in Table 2.

TABLE 2

Representative NLS Targeting Peptides

| Name | SEQ ID NO | Sequence |
| --- | --- | --- |
| NLS1 | SEQ ID NO: 16 | GGPKKKRKVEDPTG |
| Control NLS1 | SEQ ID NO: 17 | GGPKTKRKVEDPTG |
| NLS-2 | SEQ ID NO: 18 | GGGGGGPKKRKV |
| NLS-4 | SEQ ID NO: 19 | KKKKKKPKKRKV |
| M9 | SEQ ID NO: 20 | GGNQSSNFGPMKGGNFGGRSS GPYGGGQYFAKPRNQGGY |
| c-myc | SEQ ID NO: 21 | GGPAAKRVKLD |
| Nucleoplasmin | SEQ ID NO: 22 | GGKRAATKKAGQAKKKK |
| Xenopus N1 | SEQ ID NO: 23 | GGVRKKRKTEEESPLKDKDAK KSKQE |
| FGF3 | SEQ ID NO: 24 | GGRLRRDAGGRGGVYQHLGGA PRRRK |
| PARP | SEQ ID NO: 25 | GGKRKGDEVDGVDQCAKKSKK |

Fusogenic Peptides

In one aspect of the present invention, the targeting peptide comprises a fusogenic peptide. While not wishing to be bound by theory, a fusogenic peptide can be conjugated to a polynucleotide using the compounds described herein to help an internalized peptide-polynucleotide construct escape the endosome. Following internalization of peptide-polynucleotide into the cell by endocytosis, the construct must be able to escape the endosome so that the DNA may be delivered to the nucleus for gene expression. A fusogenic peptide is a peptide that acts to buffer against the endosomal proton pump to cause lysis or fuses with the endosomal membrane leading to pore formation, thereby disrupting the endosome releasing the contents to the cytosol. Therefore, the activity of the fusogenic peptide on a peptide-polynucleotide construct will aid in the release of the entire construct from the endosome. Representative fusogenic targeting peptides are shown in Table 3 and described below.

TABLE 3

Representative Fusogenic Targeting Peptides

| Name | SEQ ID NO | Sequence |
| --- | --- | --- |
| Melittin | SEQ ID NO: 26 | GGIGAVLKVLTTGLPALISWIK RKRQQ |
| Melittin (Q→E) | SEQ ID NO: 27 | GGIGAVLKVLTTGLPALISWIK RKREE |
| HA-2 | SEQ ID NO: 28 | GGLFEAIAGFIENGWEGMINGW YG |
| H5WYG | SEQ ID NO: 29 | GGLFHAIAAHFIHGGWHGLIHG WWG |
| GALA | SEQ ID NO: 30 | GGWEAALAEALAEALAEHLAEA LALEALEALEALAA |
| KALA | SEQ ID NO: 31 | GGWEAKLAKALAKALAKHLAKA LAKALAKALAA |
| JST-1 | SEQ ID NO: 32 | GGLFEALLELLESLWELLLEA |
| ppTG-1 | SEQ ID NO: 33 | GGLFKALLKLLKSLWKLLLKA |
| VSV | SEQ ID NO: 34 | GGKFTIVFPHNQKGNWKNVPSN YHY |
| Penetratin | SEQ ID NO: 35 | GGREIKIWFENRRMKWKK |
| Transportan | SEQ ID NO: 36 | GGWTLNSAGYLLGKINLKALAA LAKKIL |

In one embodiment, the fusogenic peptide may be mellitin. Melittin is an amphiphilic α-helical hemolytic peptide derived from bee venom. Melittin is a cationic peptide, allowing it to bind weakly to DNA during photolabeling, but dissociate from intramolecular binding to DNA in physiological salt.

Other examples of fusogenic peptides, include short peptides derived from the N-terminus of the influenza virus hemaglutinin HA-2. HA-2 is an acidic peptide that changes conformation to an α-helical structure when acidified in the endosome. HA-2 polylysine DNA polyplexes were able to mediate 10-10,000-fold higher gene expression over condensates without the fusogenic peptide. Mahato et al., *Curr Opin Mol Ther* (1999) 1(2): 226-243; Plank et al., *J. Biol. Chem.* (1994) 269: 12918-12924; Wagner et al., *Proc. Natl. Acad. Sci. USA* (1992) 89: 7934-7938.

Monsigny and co-workers mutated the structure of HA-2 by installing His in place of Glu to convert HA-2 into the cationic peptide H5WYG. Midoux et al., *Bioconjugate Chem.* (1998) 9: 260-267. They report that the hemolysis activity of the H5WYG is highly pH dependent with full hemolytic activity at pH 6.4. At micromolar concentrations the peptide functions similar to chloroquine in amplifying polyplex mediated gene transfer in cell culture.

GAL4 is an amphipathic peptide that transitions from random coil to an α-helical as the pH is lowered from 7.6 to 5.0. Subbarao et al., pH-dependent bilayer destabilization by an amphipathic peptide. Biochemistry (1987) 26(11): 2964-2972; Li et al., *Adv Drug Deliv Rev* (2004) 56:967-985. At physiological pH, the glutamic acid residues exhibit charge repulsion which is neutralized as the pH is lowered allowing it to adopt the α-helix structure. Parente et al., *Biochemistry* (1990) 29(37):8713-8719; Parente et al., *Biochemistry* (1990) 29(37): 8720-8728. At endosomal pH, GAL4 is able to bind to bilayer membranes and induce leakage of phosphatidylcholine vesicles. Reversal of the positions of the glutamic acid and leucine residues (LAGA) results in loss of the α-helical structure and therefore a decrease in vesicle leakage. Replacement of some Ala with Lys and a reduction in the number of Glu resulted in the cationic peptide KALA that is able to condense DNA, induce membrane leakage, and mediate gene expression. KALA behaves in the same manner as its anionic counterpart to transition from random coil to α-helix and is therefore able to retain its membrane lytic activity. Condensates prepared with KALA are able to transfect a variety of cell lines without the addition of membrane disruptive agents. Wyman et al., *Biochemistry* (1997) 36(10): 3008-3017.

JTS-1 is a novel amphipathic acidic peptide developed by Gottschalk and coworkers. The peptide lysed both phosphatidylcholine liposomes and erythrocytes at a pH of 5, and shows an 8-fold higher hemolysis activity than INF-7 (an HA-2 analogue). Gottschalk et al.: *Gene Ther.* (1996) 3: 448-457. As with GAL4, JTS-1 is negatively charged at neutral pH and unable to bind the phosphate backbone of DNA. ppTG-1 is an analogue of JTS-1 in which Glu residues were substituted to Lys. The resulting cationic peptide retains its α-helix conformation along with membrane lytic activity, but can also bind to DNA and mediate transfection in vitro, and in vivo in mice (lung) following intravenous injection. Rittner et al., *Molecular Therapy* (2002) 5(2): 104-114.

VSV is a 25 amino acid anionic peptide derived from the coat glycoprotein of the vesicular stomatitis virus. It is only active in hemolysis below pH 7. When covalently conjugated to a carrier, VSV was able to enhance receptor mediated gene transfer in vitro and in vivo. Schuster et al., *Bioconjug. Chem.* (1999) 10:1075-1083.

Penetratin is a short peptide derived from the third α-helix of the homeodomain of Antennapedia. It is only 16 amino acids in length but is able to efficiently translocate across membranes as well as the full length homeodomain protein. Derossi et al., *J. Biol. Chem.* (1994) 269(14): 10444-10450; Derossi et al., *Trends Cell Biol.* (1998) 8(2): 84-87. Penetratin has been used to transfect peptide nucleic acids, antisense oligonucleotides, and double-stranded DNAs. Deshayes et al., *Cell. Mol. Life. Sci.* (2005) 62(16): 1839-1849.

Transportan is a 27 amino acid peptide composed by joining the N-terminal sequence of the neuropeptide galanin with mastoparan, a pore-forming wasp venom peptide. Pooga et al., *FASEB J*(1998) 12: 67-77. This peptide is reported to penetrate several cell types, and once inside accumulates in the nucleoli. Pooga et al., *FASEB J.* (2001) 15(8): 1451-1453.

Receptor Ligands

Targeting peptides that target specific cell types could be used in accordance with the present invention. Although not exhaustive, the known targeting peptides shown in Table 4 could be linked covalently to polynucleotides to mediate nucleic acid delivery to these cells or tissues.

TABLE 4

Representative Receptor Ligand Targeting Peptides

| Name | Localization | SEQ ID NO | Sequence |
|---|---|---|---|
| α v Integrins | Normal/Breast Tumor Endothelium | SEQ ID NO: 37 | CDCRGDCFC |
| APN/CD13 | Normal/Breast Tumor Endothelium, Perycites | SEQ ID NO: 38 | CNGRC |
| APA | Tumor endothelium, perycites, stromal cells | SEQ ID NO: 39 | CPRECESIC |
| APP | Breast Tumor Endothelium | SEQ ID NO: 40 | CPGPEGAGC |
| MMP2 | Normal/tumor endothelium | SEQ ID NO: 41 | CTTHWGFTLC |
| MMP9 | Normal/tumor endothelium | SEQ ID NO: 42 | CRRHWGFEFC |
| NG2 | Tumor endothelium | SEQ ID NO: 43 | GLS |
| IL11-r | Prostate tumor endothelium | SEQ ID NO: 44 | CGRRAGGSC |
| Prohibitin | White fat vasculature | SEQ ID NO: 45 | CVPELGHEC |
| KDR/Flk-1 | HUVEC, tumor endothelium | SEQ ID NO: 46 | HTMYYHHYQHHL |
| VCAM-1 | Tumor endothelium | SEQ ID NO: 47 | VHSPNKK |
| Kallikrein-9 substrate | Tumor endothelium | SEQ ID NO: 48 | CSRPRRSEC |
| PDGFR | Premalignant angiogenic islet | SEQ ID NO: 49 | CRGRRST |
| RGD | | SEQ ID NO: 50 | ICRRARGDNPDDRCT |
| Integrin binding | | SEQ ID NO: 51 | PLAEIDGIELTY |

TABLE 4-continued

Representative Receptor Ligand Targeting Peptides

| Name | Localization | SEQ ID NO | Sequence |
|---|---|---|---|
| Secretin | | SEQ ID NO: 52 | HSDGTFTSELSRLRDSARLQRLLQGLV |
| GE7 (from EGF) | | SEQ ID NO: 53 | NPVVGYIGERPQYRDL |
| NL4 | | SEQ ID NO: 54 | CTTTHTFVKALTMDGKQAAWRFIRIDTAC |
| Neurotensin | | SEQ ID NO: 55 | ELYENKIPRRPYIL |
| LOX-1 binding | | SEQ ID NO: 56 | LSIPPKA |
| LOX-1 binding | | SEQ ID NO: 57 | FQTPPQL |
| LOX-1 binding | | SEQ ID NO: 58 | LTPATAI |

Peptide Hormones

The function of hormones is to serve as a signal to target cells. Accordingly, the targeting peptides of the present invention may comprise peptide hormones in order to direct polynucleotide constructs to these particular cells or tissues. Upon binding the peptide hormone receptor on the surface of these cells, the peptide may become internalized in the cell. Examples of peptide hormones which may be used as targeting peptides are shown in Table 5.

TABLE 5

Representative Peptide Hormone Targeting Peptides

| Peptide | SEQ ID NO: | Sequence |
|---|---|---|
| Oxytocin | SEQ ID NO: 59 | CYIQNCPLG |
| Vasopressin | SEQ ID NO: 60 | VYFQNCPRG |
| α-MSH | SEQ ID NO: 61 | SYSMEHFRWGKPV |
| β-MSH | SEQ ID NO: 62 | AEKKDEGPYRMEHFRWGSPPKD |
| γ-MSH | SEQ ID NO: 63 | YVMGHFRWDRFG |
| Corticotropin | SEQ ID NO: 64 | SYSMEHFRWGKPVGKKRRPVKVYPNGAEDESAEAFPLEF |
| Corticotropin releasing hormone | SEQ ID NO: 65 | SQEPPISLDLTFHLLREVLEMTKADQLAQQAHSNRKLLDIA |
| gonadotropin-releasing hormone | SEQ ID NO: 66 | EHWSYGLRPG |
| thyrotropin-releasing hormone | SEQ ID NO: 67 | EHP |
| Somatostatin | SEQ ID NO: 68 | AGCKNFFWKTFTSC |
| Calcitonin | SEQ ID NO: 70 | CSNLSTCVLGKLSQELHKLQTYPRTNTGSGTP |
| glucagon-like peptide-1 | SEQ ID NO: 71 | HAEGTFTSDVSSYLEGQAAKEFIAWLVKGRG |
| Ghrelin | SEQ ID NO: 72 | GSSFLSPEHQRVQQRKESKKPPAKLQPR |
| Obestatin | SEQ ID NO: 73 | FNAPFDVGIKLSGVQYQQHSQAL |
| Gastrin | SEQ ID NO: 74 | PGPWLEEEEEAYGWMDF |
| Secretin | SEQ ID NO: 75 | HSDGTFTSELSRLNDSARLNRLLNGLV |
| cholecystokinin, CCK | SEQ ID NO: 76 | KAPSGRVSMIKNLQSLDPSHR |

TABLE 5-continued

Representative Peptide Hormone Targeting Peptides

| Peptide | SEQ ID NO: | Sequence |
|---|---|---|
| vasoactive intestinal peptide | SEQ ID NO: 77 | HSDAVFTDNYTRLRKGMAVKKYLN SILN |
| substance p | SEQ ID NO: 78 | RPKPQQFFGLM |
| pancreatic polypeptide | SEQ ID NO: 79 | APLEPVYPGDNATPENMAQYAADL RRYINMLTRPRY |
| Peptide tyrosine-tyrosine | SEQ ID NO: 80 | YPPKPESPGEDASPEEMNKYLTAL RHYINLVTRQRY |
| neuropeptide tyrosine | SEQ ID NO: 81 | YPSKPDNPGEDAPAEDMARYYSAL RHYINLITRQRY |
| Glucagon | SEQ ID NO: 82 | HSQGTFTSDYSKYLDSRRAQD FVQWLMNT |
| angiotension II | SEQ ID NO: 83 | DRVYIHPF |

Antimicrobial Peptides

Antimicrobial peptides are short proteins, generally between 12 and 50 amino acids long (although larger proteins with similar properties such as lysozyme are often classified as antimicrobial peptides). These peptides include two or more positively charged residues provided by arginine, lysine or, in acidic environments, histidine, and a large proportion (generally >50%) of hydrophobic residues. The secondary structures of these molecules generally include (i) α-helices, (ii) β-strands due to the presence of 2 or more disulphide bonds, (iii) β-hairpins or loops due to the presence of a single disulphide bond and/or cyclization of the peptide chain, and (iv) an extended structure. Many of these peptides are unstructured in free solution, and fold into their final configuration upon partitioning into biological membranes. The ability to associate with membranes is a definitive feature of antimicrobial peptides although membrane permeabilisation is not necessary. These peptides have a variety of antimicrobial activities ranging from membrane permeabilization to action on a range of cytoplasmic targets.

The following are examples of antimicrobial peptides grouped according to structural characteristics. The targeting peptides of the present invention may include any biologically active fragment or variant of these peptides, which retain the activity of the native protein.

High content of proline, arginine, and/or phenylalanine: Abaecin, Apidaecins, Bac-5, Bac-7, Drosocin, and Prophenin.

Intramolecular disulfide bridges: α-Defensins, β-Defensins, Insect defensins, Plant defensins, Protegrins, and Drosomycin.

Amphiphilic α-helical structure: Magainins, Dermaseptins, Bombinin, Cecropin, Esculentins-1, and Esculentins-2.

Table 5 shows representative sequences of the above-named classes of antimicrobial peptides:

TABLE 5

Representative Antimicrobial Peptides

| Peptide | SEQ ID NO: | Sequence |
|---|---|---|
| Abaecin | SEQ ID NO: 84 | FVPYNPPRPGQSKPFPSFPGHGPFNPKIQWPYPLPNPPGH |
| Apidaecin | SEQ ID NO: 85 | GNRPVYIPPPRPPHPRL |
| Bac-5 | SEQ ID NO: 86 | RFRPPIRRPPIRPPFYPPFRPPIRPPIFPPIRPPFRPPLGPFPGRR |
| Bac-7 | SEQ ID NO: 87 | ALSYREAVLRAVDRINERSSEANLYRLLELDPPPKDVEDRG ARKPTSFTVKETVCPRTSPQPPEQCD |
| Drosocin | SEQ ID NO: 88 | MKFTIVFLLLACVFAMAVATPGKPRPYSPRPTSHPRPIRVRR EALAIEDHLAQAAIRPPPILPA |
| Prophenin | SEQ ID NO: 89 | AFPPPNVPGPRFPPPNFPGPRFPPPNFPGPRFPPPNFPGPRFPPP NFPGPPFPPPIFPGPWFPPPPPFRPPPFGPPRFP |
| α-Defensin | SEQ ID NO: 90 | CYCRIPACLAGERRYGTCF LGRVWAFCC |
| β-Defensin | SEQ ID NO: 91 | DHYNCVSSGGQCLYSACPIFTKIQGTCYRGKAKCCK |
| Protegrin | SEQ ID NO: 92 | RGGRLCYCRR RFCVCVGR |

TABLE 5-continued

Representative Antimicrobial Peptides

| Peptide | SEQ ID NO: | Sequence |
|---|---|---|
| Drosomycin | SEQ ID NO: 93 | DCLSGRYKGPCAVWDNETCRRVCKEEGRSSGHCSPSLKCWCEGC |
| Magainin | SEQ ID NO: 94 | DEDMDE |
| Dermaseptin | SEQ ID NO: 95 | ALWKTMLKKL GTMALHAGKA ALGAAADTIS QGTQ |
| Bombinin | SEQ ID NO: 96 | GIGALSAKGALKGLAKGLAZHFAN |
| Cecropin | SEQ ID NO: 97 | WKPFKKIEKAVRRVRDGVAKAGPAVAVVGQ AT |
| Esculentin-1 | SEQ ID NO: 98 | GIFSKLGRKKIKNLLISGLKNVGKEVGMDVVRTGIDIAGCKIKGEC |

Linkers for PL-Peptides

In some embodiments, the targeting peptides of the present invention optionally include a linker. The linker may comprise a sequence of amino acids or a polymer, e.g. PEG. The linker joins the photoaffinity label to the portion of the targeting peptide having the translocation activity. A polypeptide linker or tether sequence is typically 1 to 20 amino acids in length, preferably 2 to 10 amino acids in length. In some embodiments the linker or tether sequence is 2, 3, 4, 5, 6, 7, 8, 9, or 10 amino acid residues long. The linker sequence amino acid residues may be independently selected from any amino acid, including the naturally occurring amino acids. In some embodiments the tether amino acid sequences are independently selected from glycine, proline, and lysine. Exemplary linker sequences include Gly-Gly, poly-Gly, poly-Lys, and the like.

In suitable embodiments, the linkers exhibit improved stability and incorporate a poly-lysine chain that endows the peptide with the desirable property of allowing for the ionic binding of lysine's positively charged side chain with the negatively charge phosphate backbone of DNA. In one such embodiment, the linker comprises a tyrosine residue, followed by three (PL1) to six lysine residues (PL2).

```
PL1
PL-Tyr-Lys-Lys-Lys                  [SEQ ID NO: 99]
PL2
PL-Tyr-Lys-Lys-Lys-Lys-Lys-Lys      [SEQ ID NO: 100]
```

Polynucleotide Labeling

In another aspect, the invention provides constructs comprising a polynucleotide labeled with one or more of the compounds as described herein. In constructs of the invention, the polynucleotide can be single- or double-stranded DNA, such as a plasmid, or RNA. Constructs of the invention can have a relatively low loading of label, e.g., an average of 1 to 3 molecules of a compound of the invention polynucleotide molecule. In some embodiments, there is on average, only a single molecule of an inventive compound attached to each nucleotide molecule. Those of skill in the art will understand that in any given sample, while a plurality or even a majority of polynucleotides will be labeled with 1, 2, or 3 targeting peptides, individual polynucleotides of the sample may have lower or higher loadings of targeting peptide.

Any nucleic acid may be labeled with one or more of the compounds described herein. In some embodiments, the polynucleotide is a plasmid comprising a structural gene for use in gene therapy. For instance, the structural gene may encode a protein to replace a nonfunctional or mutant protein within the cell of a patient having a disease.

In yet another aspect, the invention provides methods of making constructs of the invention, including mixing a compound of the invention with a polynucleotide under suitable conditions to cause the polynucleotide to be covalently linked to the compound. For example, methods of making the construct include photoflashing a mixture of a polynucleotide and the compound, preferably under conditions suitable to avoid UV self-crosslinking of the polynucleotide, whereby the polynucleotide is covalently linked to the targeting peptide. The amount of targeting peptide covalently linked to the polynucleotide is controlled by adding the stoichometrically appropriate amount of peptide to plasmid. Thus, in some embodiments of the methods of making the constructs, the concentration of the compound is sufficient to provide a plurality of constructs having 1, 2 or 3 molecules of the compound attached to each polynucleotide molecule. In some embodiments, the amount of peptide added to the photolabeling reaction is from about 0.1 to about 50 pmol per fig of DNA, from about 0.1 to about 25 pmol per µg of DNA, or from about 0.1 to about than 10 pmol per µg of DNA. Preferably, the amount of peptide is about 1 pmol to about 5 pmol per µg of DNA. One of skill in the art can appreciate that the ranges provided are illustrative, and that scaling up to milligram or kilogram quantities may provide suitable amounts of photolabeled peptide-DNA for use in in vivo applications.

In an exemplary embodiment, the photolabeling of a peptide is performed by placing a microfuge vial containing the PL-peptide and polynucleotide in the center between three flash photography lamps mounted triangularly 3 inches apart. The lamps are simultaneously triggered to flash. The sample may be flashed from about 5 to about 100 times, preferably about 40 times. Other common devices, such as a fluorometer, may be used to achieve photoactivation and covalent linking.

In another aspect, the invention provides methods of localizing constructs of the invention to the cytosol or one or more subcellular compartments of a cell by contacting the cell with the construct. A cell may be contacted with the construct, wherein the activity of the targeting peptide directs the localization of the construct to the cytosol or a subcellular compartment. The methods may also comprise administering the construct in conjunction with another delivery route. For example, the construct may be delivered into the cell using various delivery routes known in the art such as targeted delivery, electroporation, or by co-administration with a cationic lipid or polyethyleneimine.

The methods may further comprise administering to a mammal a therapeutically effective amount of the construct as described herein, wherein the construct becomes localized to one or more cells or subcellular compartments of the mammal. The construct may be administered in various ways, including, but not limited to injection, aerosol or transdermally. In some embodiments of inventive methods, the mammal or mammalian cell is human, rodent (e.g. rat or mouse), non-human primate, bovine, pig, horse, dog or cat.

In some embodiments of inventive methods of localizing inventive constructs to a cell nucleus, the construct comprises a plasmid. The plasmid may include a structural gene operably linked to a promoter, and wherein the promoter directs the expression of the structural gene. In some embodiments, the structural gene comprises a reporter gene such as, but not limited to, luciferase, β-galactosidase, β-glucuronidase, or green fluorescent protein. In other embodiments, the reporter gene is luciferase. In methods where the construct includes a reporter gene such as luciferase, the methods may further include the steps of administering luciferin to the mammal and imaging the mammal to detect luciferase activity. In other embodiments of inventive methods, the plasmid further comprises a second structural gene operably linked to a second promoter. Detection of expression from the reporter gene may then be positively correlated to expression of the second structural gene.

While not wishing to be limited by theory, where the construct of the invention is a DNA-NLS conjugate, the construct is proposed to enter the nucleus via the nuclear pore complex and undergo transcription and translation. The invention is therefore applicable to the field of non-viral gene delivery in that it allows for increased gene expression for plasmid DNA delivered via a variety of routes.

The peptide polynucleotide construct of the present invention can be used to deliver many types of genes including, but not limited to reporter genes. The potential applications include enhancement of nonviral gene transfer to treat hemophilia, cancer, neuromuscular diseases, cystic fibrosis, AIDS, as well as to enhance a variety of DNA vaccines. Specific structural genes whose expression may be improved by DNA-NLS include Factor VIII and IX for treating hemophilia (GenBank Accession Nos. NP_036283 and NP_000124, respectively); combinations of plasmids expressing viral protein such as GP120 for treating AIDS by DNA vaccine (GenBank Accession No. NP_057856); DNA expressing IL12, IL15 or P53 for treating cancer (GenBank Accession Nos. NP_000873, NP_751914, NP_000537, respectively); DNS-NLS expressing dystrophin for treating muscular dystrophy (Love et al., *J. Med. Genet.* 28: 860-864 (1991)); DNA-NLS expressing CFTR for treating cystic fibrosis (Schwarz et al., *Adv. Exp. Med. Biol.* 290: 393-398 (1991)).

In other embodiments, the polynucleotide is a DNA or RNA molecule capable of mediating RNA interference (RNAi). RNAi refers to the process of sequence-specific post-transcriptional gene silencing in animals mediated by short interfering RNAs (siRNAs) (Zamore et al., 2000, Cell, 101, 25 33; Fire et al., 1998, Nature, 391, 806; Hamilton et al., 1999, Science, 286, 950 951; Lin et al., 1999, Nature, 402, 128 129; Sharp, 1999, Genes & Dev., 13:139 141; and Strauss, 1999, Science, 286, 886). RNAi can be used to interfere with gene expression in mammals.

Short interfering nucleic acids (siNAs), including siRNAs, may be administered to a cell, thereby initiating the RNAi effect against the target gene in the cell. The siNAs may comprise any single self-complementary nucleic acid strand or two complementary nucleic acid strands. The nucleic acid may be introduced in an amount which allows delivery of at least one copy per cell. Higher doses (e.g., at least 5, 10, 100, 500 or 1000 copies per cell) of double-stranded material may yield more effective inhibition; lower doses may also be useful for specific applications. Inhibition is sequence-specific in that nucleotide sequences corresponding to the duplex region of the RNA are targeted for genetic inhibition. The siNA molecule may be no more than 100 nucleotides in length, preferably no more than 80 nucleotides in length, and most preferably no more than 50 nucleotides in length. The siNA molecule may be at least 10, 12, 15, 20, 21, 22, 23, 24, 25, or 30 nucleotides in length.

siNA can be labeled using the compounds described herein and then introduced directly into a cell to mediate RNA interference (Elbashir et al., 2001, Nature 411:494 498). Many methods have been developed to make siNA, e.g, chemical synthesis or in vitro transcription. Once made, the siNAs are introduced into cells via transient transfection. Alternatively, an expression vector (i.e. a plasmid) may labeled with the compounds described herein and introduced into a cell to continually express siNAs in transiently and stably transfected mammalian cells (Brummelkamp et al., 2002 Science 296:550 553; Sui et al., 2002, PNAS 99(6): 5515 5520; Paul et al., 2002, Nature Biotechnol. 20:505 508). Some of these vectors have been engineered to express small hairpin RNAs (shRNAs), which get processed in vivo into siRNA-like molecules capable of carrying out gene-specific silencing.

Dual Peptide Labeling and Chimeric Constructs

In some embodiments, a polynucleotide is labeled with two or more targeting peptides, which may direct trafficking and localization of the polynucleotide to the cytosol and/or one or more subcellular compartments. In one such embodiment, a polynucleotide is labeled with both a fusogenic peptide and an NLS. Equal stoichiometric ratios of each targeting peptide compound may be used so that approximately the same amount of each peptide is added to the polynucleotide molecules.

In some embodiments, chimeric targeting peptides may be constructed which possess two or more peptide segments linked together in the same polypeptide chain. Each peptide segment may exhibit translocating activity by itself. Thus, the use of a peptide segment in a chimeric peptide is similar to the use of that segment singly in a targeting peptide. While not wishing to be limited by theory, if the two peptide segments direct localization to the same subcellular compartment, a synergistic effect may be observed by placing them in tandem. Alternatively, if the two peptide segments direct localization to different subcellular compartments, e.g. cytosol and nucleus, the combination of the two segments on the same chain reduces the overall number of peptides attached to DNA, thereby avoiding problems that can arise from labeling the polynucleotide with too many targeting peptides.

In one example, photolabeled chimeric peptides that contain both an NLS and a fusogenic peptide can be covalently linked to DNA. Since NLS peptides are cationic, the chimeric approach may be advantageous for incorporating anionic fusogenic peptides into DNA condensates. The fusogenic portion of the chimeric targeting peptide would help the construct escape the endosome, whereupon the NLS portion of the targeting peptide would facilitate importation of the construct to the nucleus.

EXAMPLES

Example 1

Preparation of the NLS Peptide

Plasmid DNA was derivatized with a photo-labeling NLS peptide. We prepared a NLS peptide derivatized at the N-terminus with azido tetrafluorobenzylamide (Az-TFBA) to form NLS 1 [SEQ ID NO:16] (FIG. 1) and control NLS 1 [SEQ ID NO:17]. Az-TFBA is available commercially from Invitrogen. The chemical synthesis of photolabeling NLS proved to be very efficient since the photolabel was attached during the last cycle of solid phase peptide synthesis. In each case the conjugate was purified to homogeneity on RP-HPLC and characterized by LC-MS (data not shown).

Example 2

Preparation of the NLS-Polynucleotide Conjugate

Figure 2:
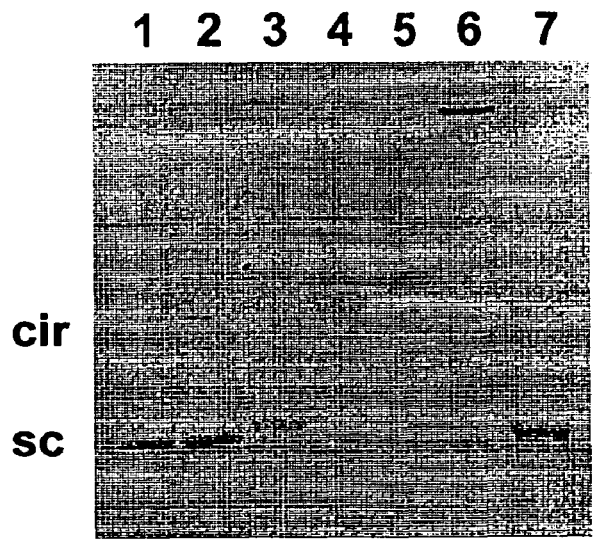
FIG. 2 presents data showing photo adducts between NLS 1 and DNA by gel electrophoresis. NLS 1 and DNA were combined and photo flashed 40 times then analyzed by agarose gel electrophoresis with ethidium bromide staining. The dramatic band shift at high NLS loading (lanes 3-6) is for illustrative purposes. The lanes represent: (1) DNA standard, (2) 0.001 nmol of NLS, (3) 0.05 nmol of NLS, (4) 0.1 nmol of NLS, (5) 0.3 nmol of NLS, (6) 0.6 nmol of NLS, (7) 0.6 nmol of NLS, no flash.

The Az-TFBA is designed to photolyse and cross-link with DNA at higher wavelengths (365 nm) than traditional photo-affinity labels, thereby avoiding UV crosslinking of DNA. A schematic representation is shown in FIG. 1. Agarose gel electrophoresis was used to establish the formation of photo adducts between NLS 1 and DNA. Combining the peptide with plasmid DNA followed by photoflash (40 times with three photo triggered flash photography lamps) resulted in a band shift of the DNA, the degree of which was dependent upon the stoichiometry of NLS to DNA (FIG. 2). The dramatic band shift at high NLS loading (lanes 3-6) is for illustrative purposes. The lanes represent: (1) DNA standard, (2) 0.001 nmol of NLS, (3) 0.05 nmol of NLS, (4) 0.1 nmol of NLS, (5) 0.3 nmol of NLS, (6) 0.6 nmol of NLS, (7) 0.6 mmol of NLS, no flash. Omitting the flashing step, even at high peptide to DNA stoichiometry, resulted in no band shift. Likewise, photo flashing DNA in the absence of peptide also did not influence the migration of DNA on gel electrophoresis. In addition, the NLS 1 photolabeled DNA bands could be stained by coomassie whereas controls (no flash or no peptide) did not stain positive.

The advantage of this strategy is that virtually any plasmid can be labeled. The number of targeting peptides bound to DNA can be controlled and synthesis of PL-DNA can be carried out on a large scale to yield sufficient quantities of nuclear targeted DNA to be used for in vivo experiments. We have conducted in vitro gene transfer studies with NLS-DNA photolabeled with varying amounts of peptide bound to determine the influence of peptide loading. We found that photo-labeling with greater than 0.05 nmols of peptide per µg of DNA completely blocks gene transfer. However, photolabeling with between 0.005 and 0.001 nmol per µg of DNA leads to optimal gene transfer.

Example 3

Quantitative Analysis of Peptide Modification of Plasmid DNA

Figure 3A:
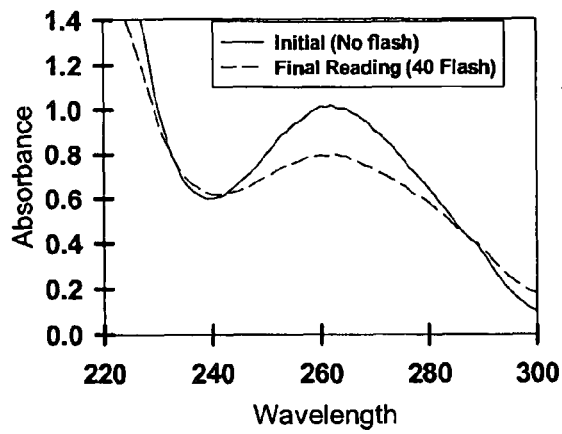
FIG. 3A shows the UV spectrum of a mixture of PL-melittin and DNA comparing a no flash control to a sample photolysed with 40 flashes.
Figure 3B:
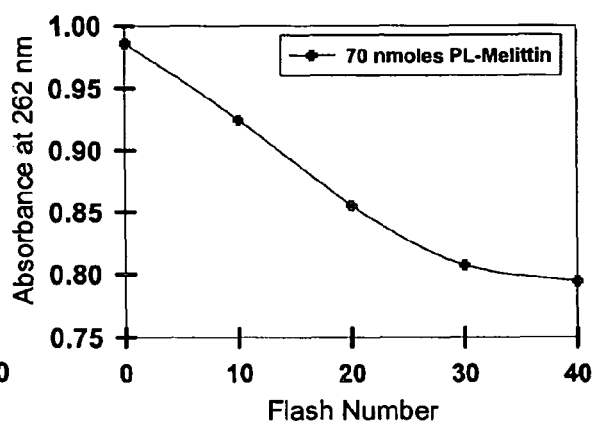
FIG. 3B is a plot showing the decrease in absorbance after 40 flashes. Readings were obtained every 10 flashes at 262 nm.

The photolabeling of a melittin peptide was performed by combining 100 µg of plasmid DNA in a microfuge vial, in total volume of 50 ul of 5 mM Hepes pH 7, with 0.01-1 nmol of PL-Mel (0.1 pmol-10 pmol per ug of DNA). The vial is placed in the center between three flash photography lamps mounted triangularly 3 inches apart. The lamps are simultaneously triggered to flash. FIGS. 3A and 3B indicate the change in the absorbance intensity of the PL label during photoflash. Absorbance at 262 nm decreases with the number of flashes as more peptide becomes bound to the DNA (FIG. 3B).

To quantify the amount of peptide covalently bound to DNA we have developed the following approach. Tyrosine-containing PL-peptides are iodinated by the chloramine T method Greenwood et al., *Biochem. J.* (1963) 89: 114-123. Briefly, 0.25 mCi of Na $^{125}$I (12.5 µl of 0.01 N NaOH) was added to 2 nmol of the PL peptide (60 µl of 0.5 M sodium phosphate buffer, pH 7.0) in a glass vial. The reaction was initiated by addition of chloramine T (20 µl of 10 mM in phosphate buffer) and allowed to react for 5 min. The reaction was quenched by the addition of sodium metabisulfite (80 µl of 10 mM in phosphate buffer).

The iodinated peptide was purified by syringe-driven solid phase extraction. The reaction mixture was loaded onto a pre-equilibrated Maxi-Clean, C18 cartridge (Alltech). Subsequently, phosphate buffered saline (or a suitable aqueous buffer) was flowed through the column to remove free Na $^{125}$I. One ml fractions were collected and gamma-counted until the readings were at a baseline. The peptide was then eluted from the cartridge with 50% acetonitrile (with PBS; v/v %) and collected in 0.5 ml fractions. The peak profile of the iodinated peptide was again determined by a gamma counter. Vacuum centrifugation was used to remove the acetonitrile, and peptide purity was determined by autoradiography of a thin layer chromatography plate. The TLC plate was developed with 90% acetic acid ($H_2O$), and quantitative densitometry was performed on a PhosphorImager (Molecular dynamics) following 24-hr autoradiographic exposure.

Figure 4:
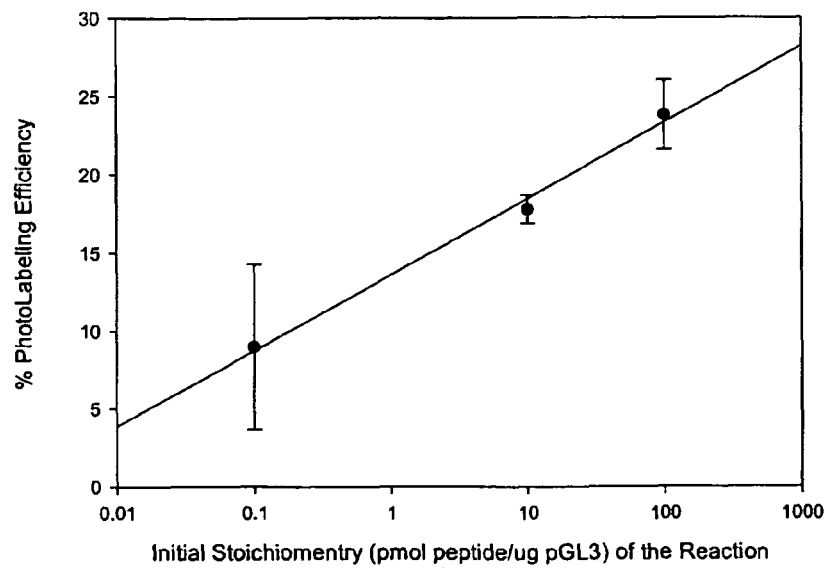
FIG. 4 presents data showing photolabeling efficiency of pGL3 as determined by using iodinated PL-NLS in the photolysis reaction.

Photolabeling efficiency is a measure of the amount of radiolabeled PL peptide that was covalently labeled to pDNA (FIG. 4). 10 µg of pDNA (25 µl of 5 mM Hepes buffer, pH 7.4) was added dropwise to a 25 µl dilution containing radiolabeled peptide (10,000 cpm) and a known quantity of the non-iodinated PL peptide in the range of 1-1000 pmol in a 1.5 ml screw-top microfuge vial. The photolabeling reaction was carried out by flashing the sample 40-times, as described above. Initial cpms of each sample were determined by a gamma-counter. Free peptide is removed by 2 successive rounds of ethanol precipitation. Briefly, 5 µl (0.1× vol.) was added to 50 µl of peptide-pDNA followed by 110 µl (2× vol.) of absolute ethanol. Samples were gently mixed by brief inversion and centrifuged (12,000×g for 15 min at 4° C.). The supernatant was carefully removed from the DNA pellet which is further washed with 150 µl of 70% ethanol. Once again, samples are centrifuged (12,000×g for 10 min at 4° C.) and the supernatant was carefully removed. The final cpms of the precipitated pellet are determined by gamma counting. Residual iodinated peptide that was not associated with pDNA, but remained in the reaction vial after washing was accounted for by a control reaction containing no pDNA. Likewise, the amount of iodinated peptide that was ionically bound to pDNA is determined by a non-photoflashed control.

Example 3

Nuclear Localization of NLS-DNA In Vitro

Confocal fluorescence microscopy was used to evaluate the ability of NLS-DNA to target the nucleus relative to a control. pGL3 (a plasmid encoding Luciferase) was covalently labeled with the fluorophore Cy3. The plasmid was purified by ethanol precipitation and analyzed by gel electrophoresis and scanning fluorescence to confirm covalent attachment of the fluorophore. Cy3 labeled pGL3 was then further modified by photolabeling with either NLS 1 or control NLS 1.

Figure 5:
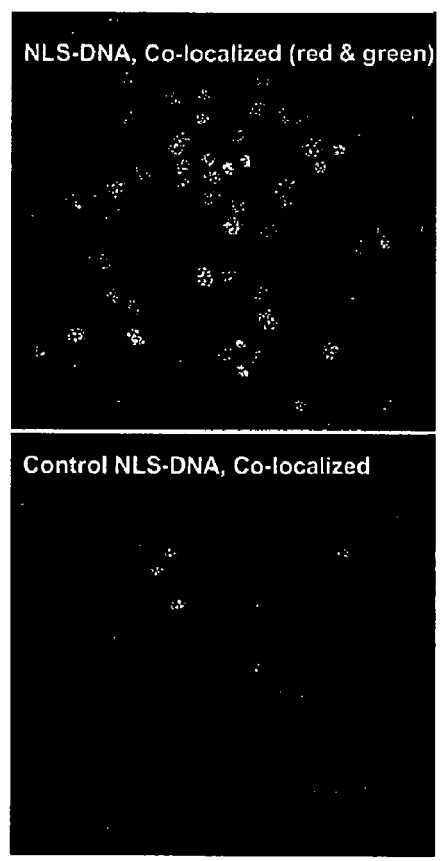
FIG. 5 shows confocal fluorescence microscopic images of NLS-DNA (upper panel) and control cNLS-DNA (lower panel) administered to 3T3 cells. Both samples were photolabeled with 0.004 nmol of peptide per µg of DNA labeled with Cy3 (green emitting fluorophore) and nuclei stained with TO-PRO-3 (red emitting fluorophore). The black and white images illustrate the co-localization of green and red pixels.

The doubly labeled plasmid (2 μg) was condensed with PEI (polyethylene imine) (9:1, N:P) and used to transfect 3T3 cells in DMEM (2% FBS) for 6 hrs, followed by three washes with PBS and fixing with 4% paraformaldehyde. Cells were maintained at 4° C. in the dark in PBS until imaged. Just prior to imaging, the cells were permeablized with 0.5% Triton X-100 and treated with TO-PRO-3 to stain the nuclei. The confocal fluorescence imaging was performed on a Bio-Rad Radience 2100MP Multiphoton/Confocal Microscope. Image analysis was performed using NIH Image J software. The results suggest a much stronger nuclear localization when using DNA labeled with NLS 1 versus control NLS 1 (FIG. 5). Although not quantitative, the black and white co-localization micrographs suggest more Cy3-DNA overlaps with TO-PRO-3 nuclear stain when using NLS compared to control NLS.

Figure 6:
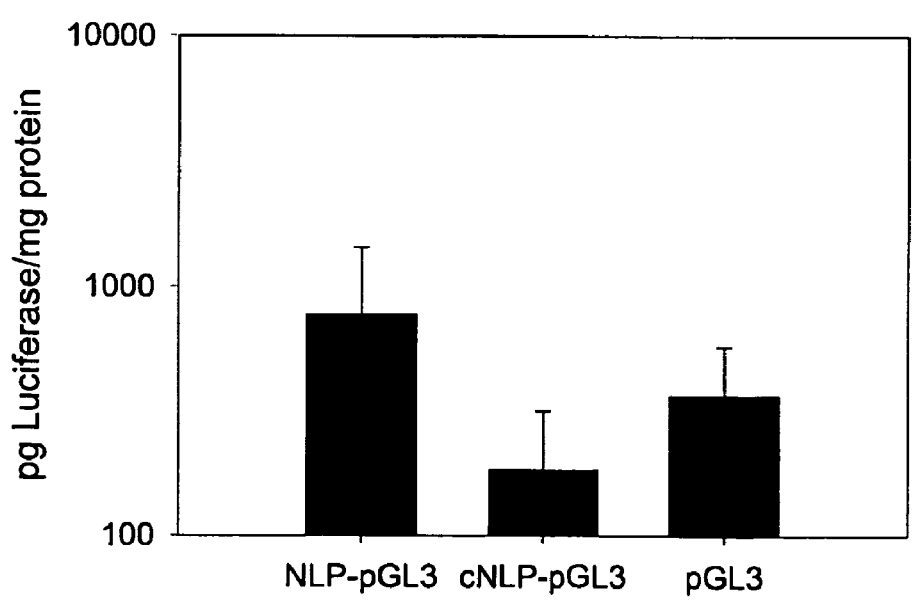
FIG. 6 presents data showing gene transfer efficiency using NLS-DNA. The PEI mediated gene transfer efficiency of pGL3 was evaluated in 3T3 cells.

To support the conclusion that the NLS-DNA conjugates are entering the nucleus, luciferase gene expression in vitro was examined. FIG. 6 presents data showing gene transfer efficiency using NLS-DNA. The PEI mediated gene transfer efficiency of pGL3 was evaluated in 3T3 cells. The plasmid was photolabeled with 0.004 nmols of NLS 1 (NLP) or control NLS 1 (cNLP) and compared to unmodified pGL3 (pDNA). The results represent the mean and standard deviation of three independent transfections. Cells transfected with the NLP-pGL3 construct exhibited significantly greater luciferase expression than cNLP-pGL3 or pGL3 alone.

Example 4

In Vivo Gene Transfer by NLS DNA

Figure 7A:
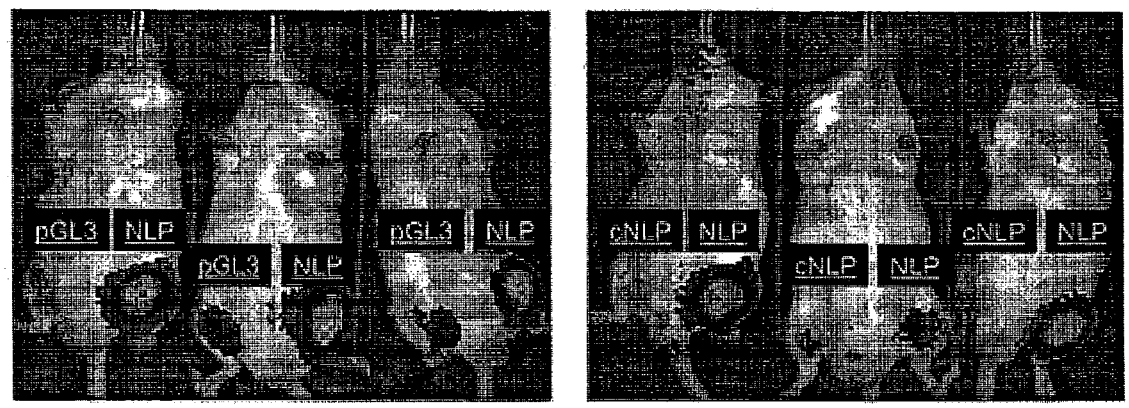
FIG. 7A shows in vivo analysis of luciferase expression of NLS-DNA and cNLS-DNA by bioluminescence imaging.
Figure 7B:
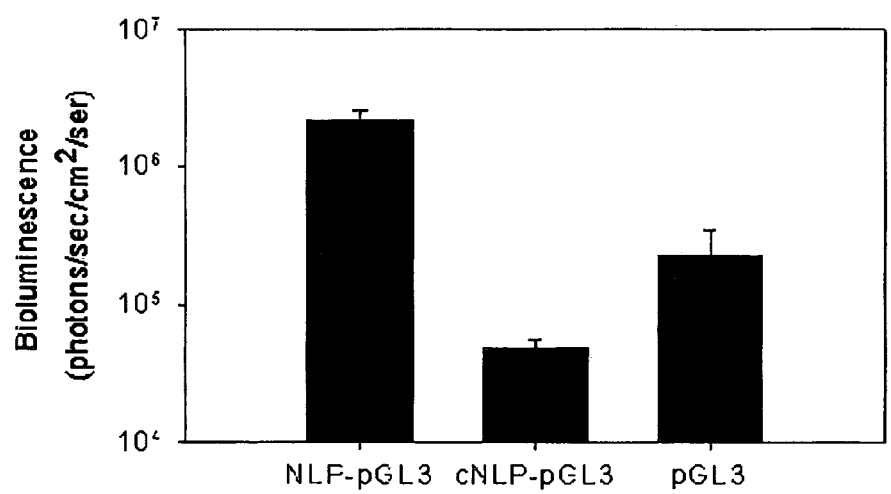
FIG. 7B is a quantitative representation of the bioluminescence data shown in FIG. 7A.

To demonstrate that NLS-DNA would also show enhanced gene expression in vivo, mice (in triplicate) were given an intramuscular (i.m.) dose of 20 μg of NLS 1-DNA (NLP), control-NLS-DNA (cNLP) or unmodified DNA (pGL3) in 20 μl of PBS. The mice were imaged after 24 hours by interperitoneal (i.p.) administration of luciferin (2.4 mg in 80 μl of PBS), followed by measuring the luciferase read out using bioluminescence imaging (BLI). The results shown in FIG. 6A illustrate mice after 1 day and show that luciferase expression was increased in mice dosed with NLS-DNA relative to cNLS-DNA or DNA. The images generated in FIG. 7A were quantified by integrating the bioluminescene read out (FIG. 7B). The data indicates a more than 10-fold increase in gene expression mediated by NLS-DNA relative to controls with statistical significance of $p<0.005$.

A second experiment analyzed two additional NLS sequences. pGL3 was labeled with PL-NLS-2 or PL-NLS-4 by the photolabeling methods described above. Briefly, 0.5-50 pmol NLS (12.5 μl in 5 mM hepes buffer, pH 7.4) was added dropwise, while vortexing, to 5 μg pGL3 (12.5 μl hepes buffer). Samples were photoflashed 40-times and subsequently diluted up to 125 μl with $H_2O$. Further dilution with 125 μl of 2× normal saline allowed for in vivo doses of 1 μg pGL3 to be dosed in 50 μl of normal saline.

Male ICR mice (Harlan) were used for in vivo dosing in a subsequent bioluminescent imaging assay. Briefly, mice were anesthetized by a 200 μl intraperitoneal dose of ketamine/xylazine (20 mg/ml and 20 mg/ml, respectively). The ventral lower hind limbs were shaved with a shearing scissors and swabbed with ethanol. The intramuscular (im) dose of pGL3 (1 μg in 50 μl normal saline) was delivered to the gastrocnemius via a 1 cc, 28 G×½ single injection syringe. Depth of administration was controlled with a piece of Teflon tubing that sheaths the needle, leaving 3-4 mm exposed. The im dose was delivered over the course of 10 sec followed by a 10 sec pause before slowly removing the needle from the muscle.

Electroporation of the im dose was carried out by the ECM 830 Square Wave Electroporation System. One min following the pGL3 dose, the 2-needle electrode array was positioned straddling the site of injection and pressed slightly into the gastrocnemius. The power source was initialized to deliver 6 successive stimuli, each 100 V in intensity and 20 ms in duration. There was a 100 ms interval between stimuli. After electroporation, mice were allowed to recover from the anesthetic before being returned to the animal care facility.

Figure 8A:
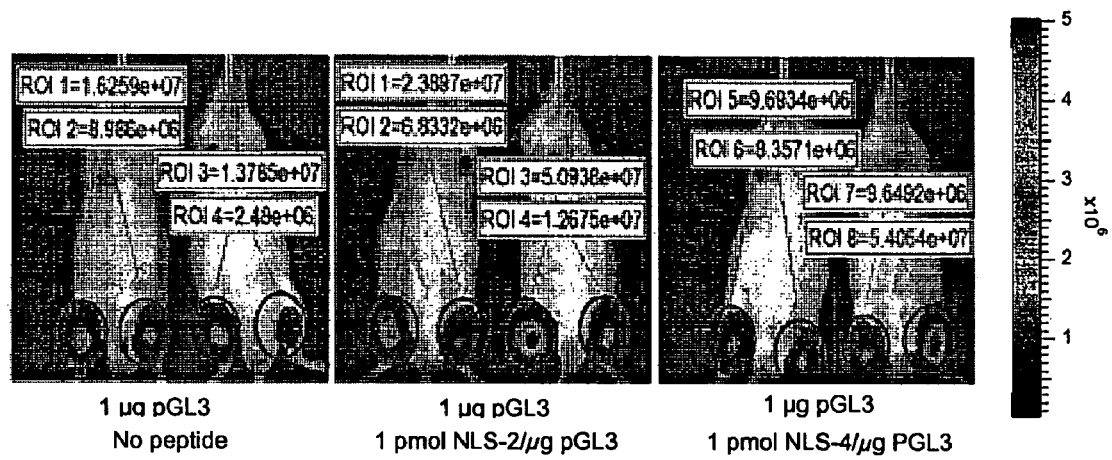
FIG. 8A shows an in vivo analysis of luciferase expression of NLS-2 and NLS-4 at an initial reaction stoichiometry of 1 pmol of peptide per µg of pGL3.
Figure 8B:
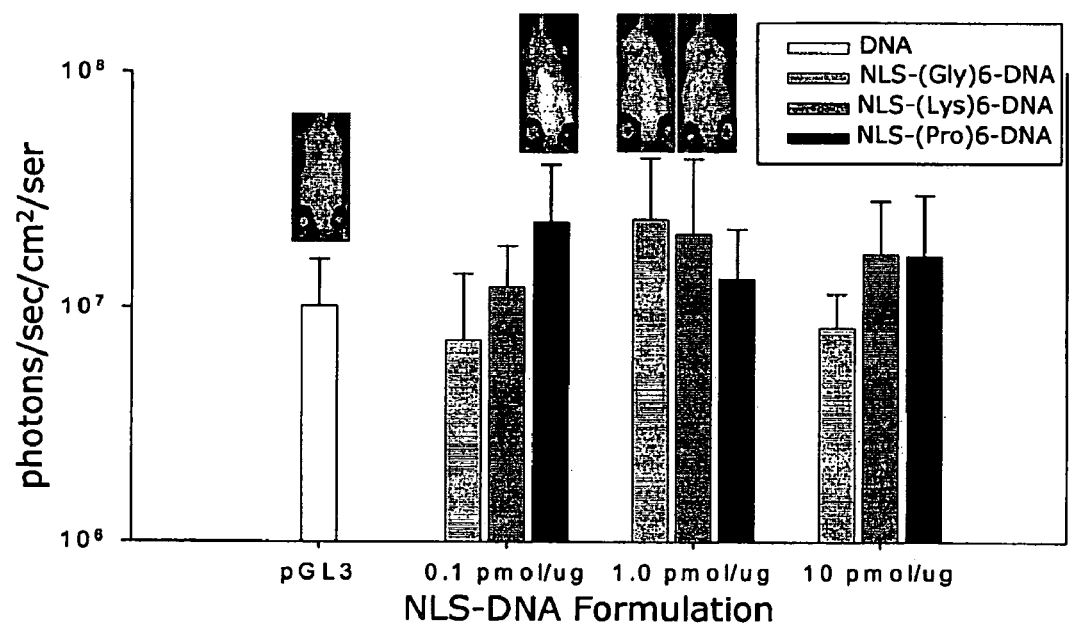
FIG. 8B is a quantitative representation of bioluminescence data comparing luciferase expression in vivo from NLS constructs having varying linkers: NLS-(Gly)6 DNA (peptide disclosed as SEQ ID NO: 101), NLS-(Lys)6 DNA (peptide disclosed as SEQ ID NO: 102), and NLS-(Pro)6 DNA (peptide disclosed as SEQ ID NO: 103).

Luciferase expression from im dosing was quantified using the IVIS system for bioluminescent imaging (FIG. 8A). Mice can be initially imaged 24 hr following pGL3 dose. Briefly, mice were anesthetized by isofluorane and remained under anesthetic in the imaging chamber via a gas-flow manifold. Once in the imaging chamber, 40 μl of luciferin (30 mg/ml) was dosed locally at the pGL3 injection site using the same type of 1 cc, 28 G×½ syringe as noted above. Images were acquired 10 min following the luciferin dose with the following fixed conditions: 0.2 second photographic acquisition time, 30 second bioluminescence acquisition time, medium binning, 24.6×24.6 cm field of view. Biolumenescent intensity was integrated and quantified using the Igor Pro software. The results shown in FIG. 7A were quantified by integrating the bioluminescence read out (FIG. 8B). The data indicates a significant increase in luciferase expression in mice dosed with either NLS-(Gly)6-DNA (peptide disclosed as SEQ ID NO: 101), NLS-(Lys)6-DNA (peptide disclosed as SEQ ID NO: 102), NLS-(Pro)6-DNA (peptide disclosed as SEQ ID NO: 103) compared to the unmodified plasmid.

Example 5

Photolabeled Melittin Peptides

Using automated solid phase peptide synthesis, we synthesized and characterized photolabeled melittin (PL-Mel) or PL-Mel-Y (an analogue with a C-terminal Tyr for the purpose of iodination). As with NLS, we have attached the photolabel (PL) on the N-terminus of the peptide. As with NLS-DNA, PL-Mel binds ionically with DNA and reacts covalently upon flash photolysis. This covalent attachment also results in a band shift on gel electrophoresis with increasing amounts of PL-Mel (data not shown).

Figure 9:
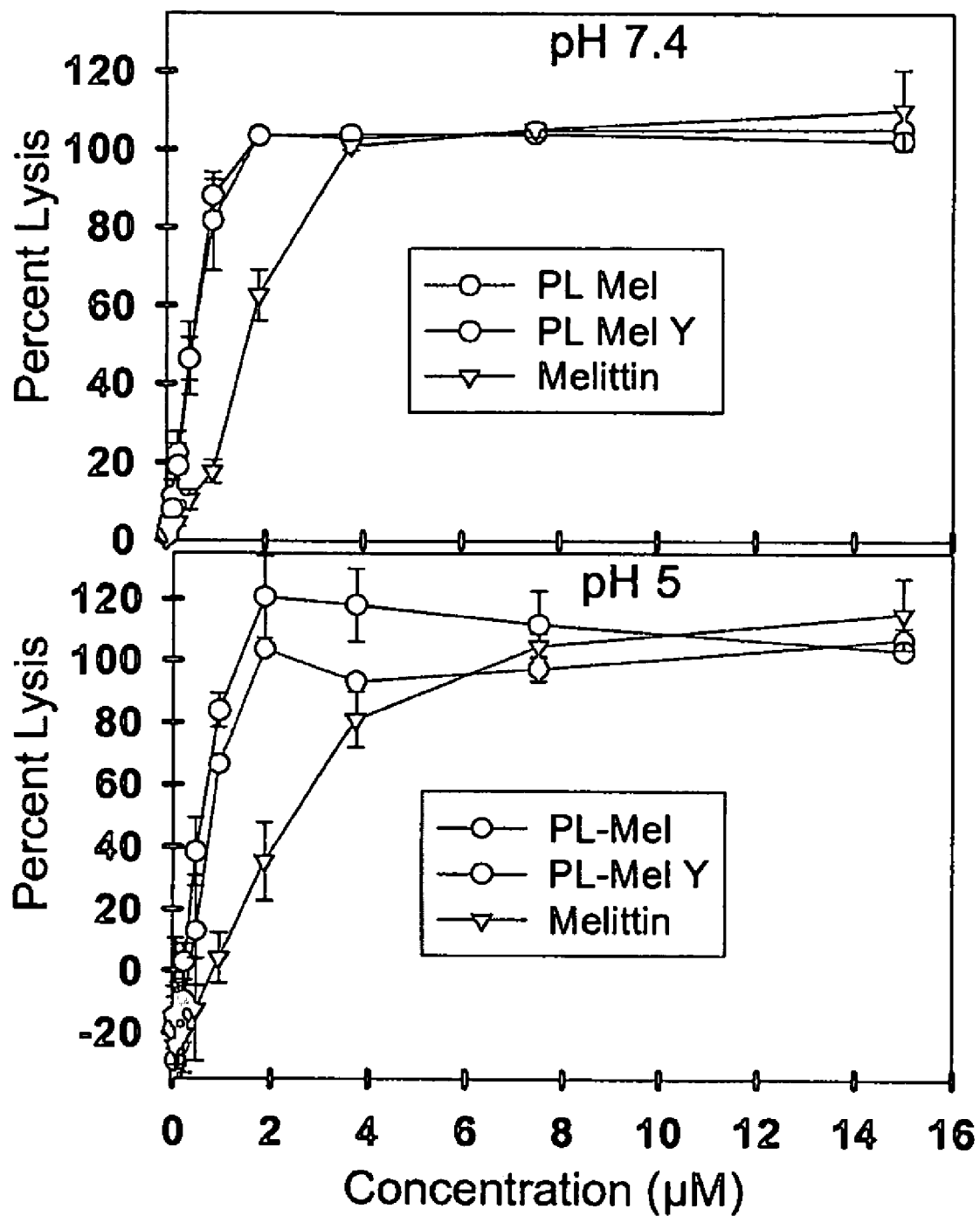
FIG. 9 presents data showing the hemolytic activity of photolabelled melittin compared to natural melittin at pH 7.4 (upper panel) and pH 5.0 (lower panel)

The following example shows that PL-Mel and PL-Mel Y remain fully active in a RBC lysis assay compared to natural melittin (FIG. 9). In a 96-well filter plate, $7×10^6$ freshly isolated mouse RBCs were added to a titration of 0-15 μM of peptide in 50 μl of PBS pH 7.4 (upper panel) or at pH 5.0 (lower panel). After 30 min at 37° C., the cells were suction filtered and the hemoglobin in the filtrate was measured by absorbance at 410 nm. The percent hemolysis was calculated relative to controls of complete lysis and zero lysis, performed by incubating RBCs in either water or PBS, respectively.

pGL3 (0.5 μg) was diluted with 5 mM Hepes, pH 7.4 to a final volume of 500 μl. PL Melittin (1 nmol/ml) was added to pGL3 then flashed 40 times with the photo flash apparatus. After flashing, the labeled DNA samples are stored in the dark for 30 min at 4° C. The PL-Mel-DNA samples were combined with normal saline to achieve a volume equal to 9% of the mouse body weight (approximately 1.5 ml). Triplicate mice were dosed i.v. tail vein in 5 seconds using a 27 gauge needle.

Gene expression was quantified after 24 hours by bioluminescent imaging (BLI), in which mice are dosed intraperitoneally with 80 μl of 30 mg/ml D-luciferin solution and anesthetized with a 3% isofluorane solution to allow for immobilization and proper positioning to be imaged with an intensified CCD camera (IVIS imaging 200 series, Xenogen). After imaging, expression is quantified as photons/second/cm$^2$/sr using the Living Image 2.50 software supplied by Xenogen and data processing is completed through using Sigma Plot 9.0 (Systat Software, Inc).

Figure 10:
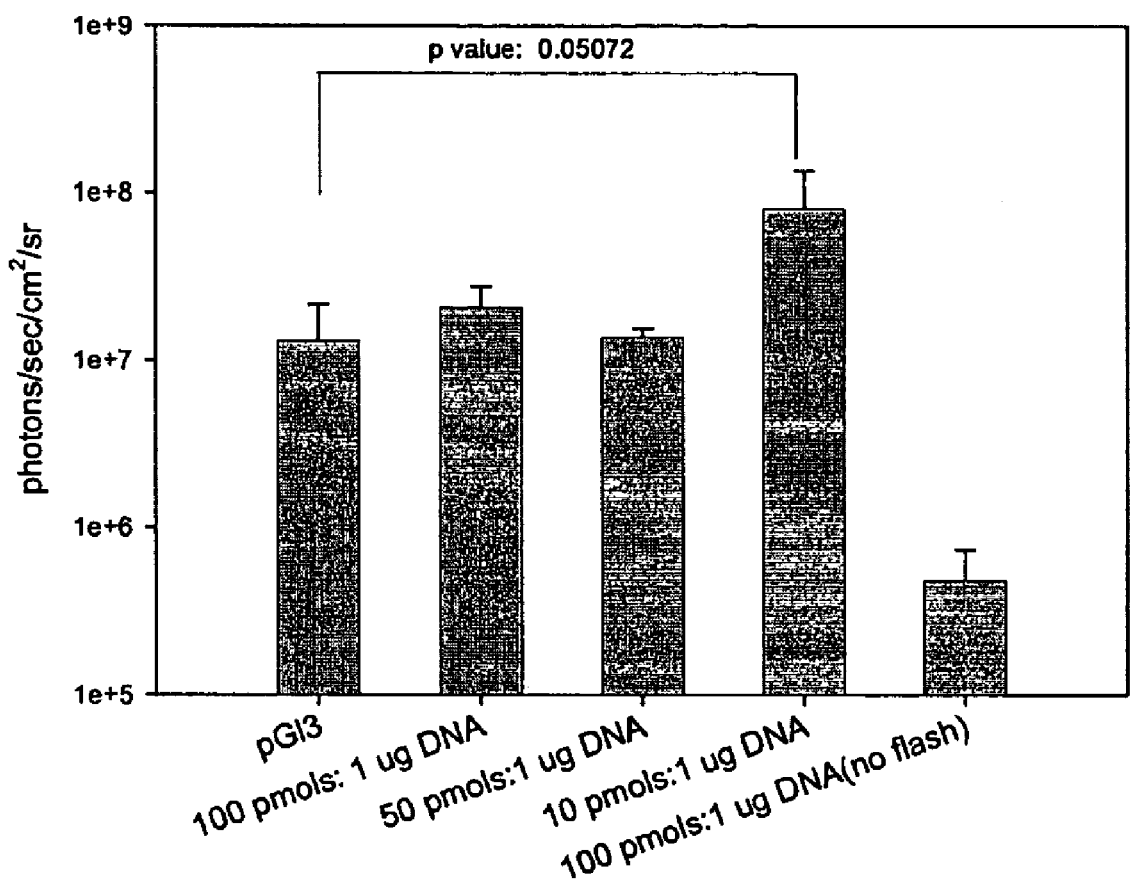
FIG. 10 presents data showing enhanced transgene expression of luciferase following photolabeling of pGl3 with PL-Melittin at various stoichiometric ratios of PL-peptide:DNA.

The results are shown in FIG. 10 and demonstrate a statistically significant 6-fold increase in gene transfer efficiency for PL-Mel-pGL3 relative to pGL3 control or PL-Mel-pGL3 where the flash was omitted. This result is important because it establishes that covalent modification of pGL3 with a fusogenic peptide can significantly improve gene transfer. Thereby NLS and PL-Mel are able to increase gene transfer by independent mechanisms, suggesting that optimal NLS and fusogenic peptides may work synergistically to improve gene transfer efficiency.

Example 6

C-Versus N-Terminal Labeling of Peptides

A C-terminal photolabeled melittin may be prepared by attaching FMOC 4-azido-1,2,4,5 tetrafluoro phenylalanine (PL) to Wang resin. A two Gly linker can be added and the 26 amino acid melittin peptide synthesis can be conducted on the resin. As with the N-terminal photolabeled melittin described in Example 5, Gln 25 and 26 can be substituted with glutamic acid. A comparison between the compounds where the photolabel is attached at the N-terminus or C-terminus can be made to ascertain the relative efficiency of the two compounds in mediating the translocation of a polynucleotide construct from the endosome to the cytosol.

Example 7

Peptide Linkers

Incorporating a poly-lysine chain as a linker between the photolabel and the targeting peptide allows for the ionic binding of the Lys positively charged side chain and the negatively charged phosphate backbone of DNA. However, peptides containing a three-lysine linker were found to be prone to degradation without photolabel stimulation (data not shown).

To overcome the instability issue, a tyrosine residue was positioned between the photolabel and the poly-lysine portion PL1 (SEQ ID NO:99) of the linker in an effort to sterically hinder the photolabel's attack of the ε amine of lysine upon activation. The incorporation of the tyrosine has the added benefit of allowing quantitation of photolabeling efficiency. That is, the phenol side chain enables the incorporation of $^{125}$I onto the peptide to be used as a radioactive tracer in which to conduct precise and accurate labeling studies in which the photolabeling efficiency can be determined quantitatively.

Figure 11:
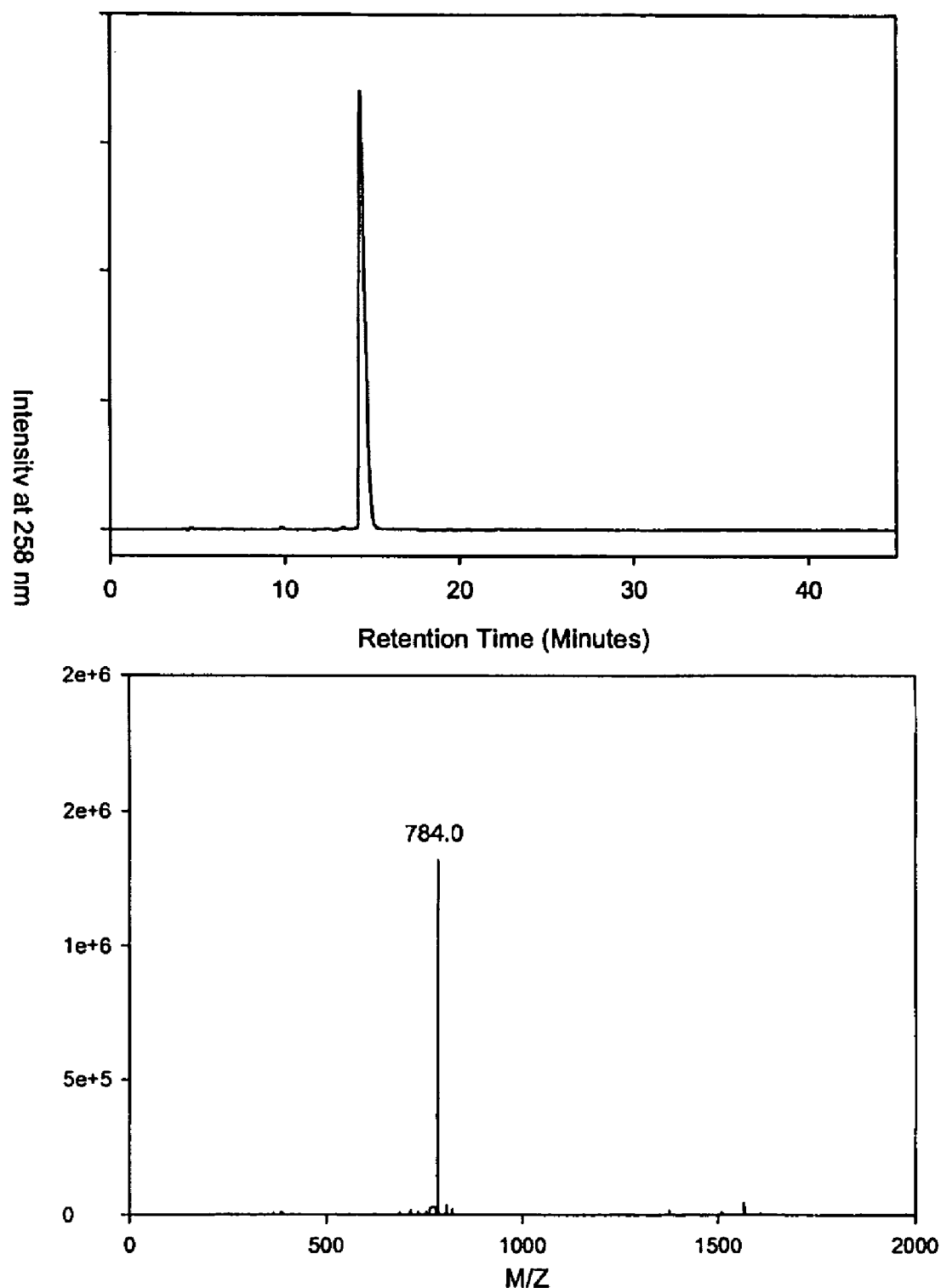
FIG. 11 shows LC-MS data of a photolabel linker. The upper panel shows the RP-HPLC purity and the bottom panel illustrates the pass of the linker peptide.

To test the hypothesis that the new linker would be stable under normal operating conditions, the linker was first synthesized via solid phase peptide synthesis and then purified by preparative reverse phase HPLC. Characterization and purity of the linker was accomplished through analytical reverse phase HPLC and LC/MS (FIG. 11). The stability of the linker peptide was determined by LC/MS after exposure to a variety of conditions including incubations at room temperature, 37° C., 50° C., and exposure to sunlight.

Based on the LC/MS results and comparison against an untreated control consisting of only PL-L1, the model peptide appears to stable when exposed to a variety of conditions with the exception that the sunlight exposed samples demonstrated moderate degradation as indicated by the LC/MS data. However, this is not surprising since PL-L1 peptide is a photoactive compound and should photoactivate if provided the proper stimulus.

Example 8

Chimeric Peptides and Dual-Labeled Polynucleotides

Dual peptide-DNA and chimeric peptide-DNA may be analyzed by hydrodynamic and muscle dosing as described above. Targeting peptides comprising an NLS and a fusogenic peptide may be used in the constructs. Since each peptide was individually active in enhancing expression during either muscle dosing or hydrodynamic dosing, a synergistic enhancement in gene expression is anticipated from the combination.

What is claimed is:

1. A compound comprising the following structure:

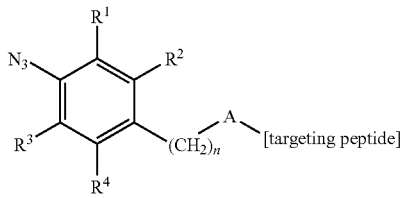

where $R^1$, $R^2$, $R^3$, and $R^4$ are F;
n is 1;
A is CO or NH;
wherein the targeting peptide is a peptide that can translocate and localize to the cytosol or a subcellular compartment of a cell; and
wherein the targeting peptide is selected from the group consisting of NLS peptides, fusogenic peptides, receptor ligands, antimicrobial peptides, and peptide hormones.

2. The compound of claim 1, wherein the targeting peptide has an N-terminus and a C-terminus, and when A is CO, A forms an amide bond with an α-amino group of the N-terminal amino acid residue of the targeting peptide, and when A is NH, A forms an amide bond with the α-carboxyl group of the C-terminal amino acid residue of the targeting peptide.

3. The compound of claim 1, wherein the sequence of the targeting peptide is about 5 to about 50 amino acid residues long.

4. The compound of claim 1, wherein the NLS peptide is a fragment of a protein selected from the group consisting of SV40 large T NLS, M9 NLS, c-myc NLS, nucleoplasmin NLS, Xenopus N1 NLS, FGF3 NLS, and PARP NLS, or a variant having at least 95% amino acid sequence identity to the fragment.

5. The compound of claim 1, wherein the NLS peptide comprises a sequence having at least 95% amino acid sequence identity to SEQ ID NOS: 16-25.

6. The compound of claim 1, wherein the fusogenic peptide is a fragment of a protein selected from the group consisting of melittin, HA-2, H5WYG, GAL4, KALA, JST-1, ppTG-1, VSV, penetratin, and transportan.

7. The compound of claim 1, wherein the fusogenic peptide comprises a sequence having at least 95% amino acid sequence identity to SEQ ID NOS: 26-36.

8. The compound of claim 1, wherein the receptor ligand comprises a sequence having at least 95% amino acid sequence identity to SEQ ID NOS: 37-58.

9. The compound of claim 1, wherein the antimicrobial peptide is a fragment of a protein selected from the group consisting of: Abaecin, Apidaecins, Bac-5, Bac-7, Drosocin, Phosphenin, α-Defensins, β-Defensins, Insect defensins, Plant defensins, Protegrins, Drosomycin, Amphiphilic α-helical structure: Magainins, Dermaseptins, Bombinin, Cecropin, Esculentins-1, and Esculentins-2, or a variant having at least 95% amino acid sequence identity to the fragment.

10. The compound of claim 1, wherein the peptide hormone comprises a sequence having at least 95% amino acid sequence identity to SEQ ID NOS: 59-83.

11. The compound of claim 1, wherein the targeting peptide comprises a linker of 1 to 10 amino acid residues.

12. The compound of claim 11, wherein the linker comprises SEQ ID NO: 99 or 100.

13. A method comprising photoflashing a mixture of a polynucleotide and the compound of claim 1 under conditions suitable to avoid UV self-crosslinking of the polynucleotide, whereby the polynucleotide is covalently linked to the targeting peptide through the photoaffinity label.

14. The method of claim 13, wherein the concentration of the compound is sufficient to provide a construct having 1 to 3 molecules of the compound attached to the polynucleotide.

15. The method of claim 13, wherein the mixture comprises about 0.1 to about 10 pmol of the compound per µg of the polynucleotide.

* * * * *

UNITED STATES PATENT AND TRADEMARK OFFICE
CERTIFICATE OF CORRECTION

PATENT NO. : 7,795,380 B2
APPLICATION NO. : 11/757848
DATED : September 14, 2010
INVENTOR(S) : Kevin G. Rice, Garrett R. Rettig and Nicholas J. Baumhover It is certified that error appears in the above-identified patent and that said Letters Patent is hereby corrected as shown below:

In the Claim Section amend the claims as follows:

Col. 73, in Claim 4, lines 36-38 of the Patent, please delete ", or a variant having at least 95% amino acid sequence identity to the fragment".

Col. 74, in Claim 6, line 3 of the Patent, please delete "GAL4" replace with GALA.

Col. 74, in Claim 9, lines 18-19 of the Patent, please delete ", or a variant having at least 95% amino acid sequence identity to the fragment".

Signed and Sealed this

Fourteenth Day of December, 2010

David J. Kappos
*Director of the United States Patent and Trademark Office*

SEQUENCE LISTING

```
<160> NUMBER OF SEQ ID NOS: 108

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Lys Lys Lys Arg Lys Val
1               5

<210> SEQ ID NO 2
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 2

Arg Arg Lys Arg Gln Arg
1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(13)
<223> OTHER INFORMATION: variable 11 amino acid linker

<400> SEQUENCE: 3

Lys Arg Xaa Xaa Xaa Xaa Xaa Xaa Xaa Xaa Xaa Xaa Xaa Lys Lys Leu
1               5                   10                  15

Arg

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(17)
<223> OTHER INFORMATION: variable 12 amino acid linker

<400> SEQUENCE: 4

Arg Lys Lys Arg Lys Xaa Xaa Xaa Xaa Xaa Xaa Xaa Xaa Xaa Xaa Xaa
1               5                   10                  15

Xaa Lys Lys Ser Lys
            20

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Asn Lys Ile Pro Ile Lys Asp Leu Leu Asn Pro Gln
1               5                   10

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Tyr Leu Thr Gln Glu Thr Asn Lys Val Glu Thr Tyr Lys Glu Gln Pro
1               5                   10                  15
```

```
Leu Lys Thr Pro Gly Lys Lys Lys Gly Lys Pro
            20                  25
```

```
<210> SEQ ID NO 7
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
            35
```

```
<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ser Ala Asn Lys Val Thr Lys Asn Lys Ser Asn Ser Ser Pro Tyr Leu
1               5                   10                  15

Asn Lys Arg Lys Gly Lys Pro Gly Pro Asp Ser
            20                  25
```

```
<210> SEQ ID NO 9
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Val His Ser His Lys Lys Lys Ile Arg Thr Ser Pro Thr Phe Thr
1               5                   10                  15

Thr Pro Lys Thr Leu Arg Leu Arg Arg Gln Pro Lys Tyr Pro Arg Lys
            20                  25                  30

Ser Ala Pro Arg Arg Asn Lys Leu Asp His Tyr
            35                  40
```

```
<210> SEQ ID NO 10
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asn Ala Pro Ser Ala Lys Ala Thr Ala Ala Lys Lys Ala Val Val Lys
1               5                   10                  15

Gly Thr Asn Gly Lys Lys Ala Leu Lys Val Arg Thr Ser Ala Thr Phe
            20                  25                  30

Arg Leu Pro Lys Thr Leu Lys Leu Ala Arg
            35                  40
```

```
<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Pro Ala Ala Lys Arg Val Lys Leu Asp
1               5

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Lys Arg Pro Ala Ala Thr Lys Lys Ala Gly Gln Ala Lys Lys Lys Lys
1               5                   10                  15

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Val Arg Lys Lys Arg Lys Thr Glu Glu Glu Ser Pro Leu Lys Asp Lys
1               5                   10                  15

Asp Ala Lys Lys Ser Lys Gln Glu
            20

<210> SEQ ID NO 14
<211> LENGTH: 24
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Arg Leu Arg Arg Asp Ala Gly Gly Arg Gly Gly Val Tyr Glu His Leu
1               5                   10                  15

Gly Gly Ala Pro Arg Arg Arg Lys
            20

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Lys Arg Lys Gly Asp Glu Val Asp Gly Val Asp Glu Cys Ala Lys Lys
1               5                   10                  15

Ser Lys Lys
```

-continued

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Gly Pro Lys Lys Lys Arg Lys Val Glu Asp Pro Thr Gly
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Gly Pro Lys Thr Lys Arg Lys Val Glu Asp Pro Thr Gly
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gly Gly Gly Gly Gly Gly Pro Lys Lys Arg Lys Val Gly
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Lys Lys Lys Lys Lys Lys Pro Lys Arg Lys Val Gly
1               5                   10

<210> SEQ ID NO 20
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gly Gly Asn Gln Ser Ser Asn Phe Gly Pro Met Lys Gly Gly Asn Phe
1               5                   10                  15

Gly Gly Arg Ser Ser Gly Pro Tyr Gly Gly Gln Tyr Phe Ala Lys
                20                  25                  30

Pro Arg Asn Gln Gly Gly Tyr
            35

<210> SEQ ID NO 21
<211> LENGTH: 11

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Gly Pro Ala Ala Lys Arg Val Lys Leu Asp
1               5                  10

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gly Gly Lys Arg Ala Ala Thr Lys Lys Ala Gly Gln Ala Lys Lys Lys
1               5                  10                  15

Lys

<210> SEQ ID NO 23
<211> LENGTH: 26
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gly Gly Val Arg Lys Lys Arg Lys Thr Glu Glu Glu Ser Pro Leu Lys
1               5                  10                  15

Asp Lys Asp Ala Lys Lys Ser Lys Gln Glu
            20                  25

<210> SEQ ID NO 24
<211> LENGTH: 26
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gly Gly Arg Leu Arg Arg Asp Ala Gly Gly Arg Gly Gly Val Tyr Gln
1               5                  10                  15

His Leu Gly Gly Ala Pro Arg Arg Arg Lys
            20                  25

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Gly Lys Arg Lys Gly Asp Glu Val Asp Gly Val Asp Gln Cys Ala
1               5                  10                  15

Lys Lys Ser Lys Lys
            20
```

```
<210> SEQ ID NO 26
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Gly Ile Gly Ala Val Leu Lys Val Leu Thr Thr Gly Leu Pro Ala
1               5                   10                  15

Leu Ile Ser Trp Ile Lys Arg Lys Arg Gln Gln
            20                  25

<210> SEQ ID NO 27
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Gly Ile Gly Ala Val Leu Lys Val Leu Thr Thr Gly Leu Pro Ala
1               5                   10                  15

Leu Ile Ser Trp Ile Lys Arg Lys Arg Glu Glu
            20                  25

<210> SEQ ID NO 28
<211> LENGTH: 24
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Gly Leu Phe Glu Ala Ile Ala Gly Phe Ile Glu Asn Gly Trp Glu
1               5                   10                  15

Gly Met Ile Asn Gly Trp Tyr Gly
            20

<210> SEQ ID NO 29
<211> LENGTH: 25
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Gly Leu Phe His Ala Ile Ala Ala His Phe Ile His Gly Gly Trp
1               5                   10                  15

His Gly Leu Ile His Gly Trp Trp Gly
            20                  25

<210> SEQ ID NO 30
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Gly Trp Glu Ala Ala Leu Ala Glu Ala Leu Ala Glu Ala Leu Ala
```

```
                    1               5              10             15
Glu His Leu Ala Glu Ala Leu Ala Glu Ala Glu Ala Leu Glu Ala Leu
                   20              25              30
Ala Ala

<210> SEQ ID NO 31
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Gly Trp Glu Ala Lys Leu Ala Lys Ala Leu Ala Lys Ala Leu Ala
1               5                  10                  15
Lys His Leu Ala Lys Ala Leu Ala Lys Ala Leu Ala Lys Ala Leu Ala
                   20              25              30
Ala

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gly Gly Leu Phe Glu Ala Leu Leu Glu Leu Leu Glu Ser Leu Trp Glu
1               5                  10                  15
Leu Leu Leu Glu Ala
                   20

<210> SEQ ID NO 33
<211> LENGTH: 21
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Gly Leu Phe Lys Ala Leu Leu Lys Leu Leu Lys Ser Leu Trp Lys
1               5                  10                  15
Leu Leu Leu Lys Ala
                   20

<210> SEQ ID NO 34
<211> LENGTH: 25
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Gly Lys Phe Thr Ile Val Phe Pro His Asn Gln Lys Gly Asn Trp
1               5                  10                  15
Lys Asn Val Pro Ser Asn Tyr His Tyr
                   20              25

<210> SEQ ID NO 35
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gly Gly Arg Glu Ile Lys Ile Trp Phe Glu Asn Arg Arg Met Lys Trp
1               5                   10                  15

Lys Lys

<210> SEQ ID NO 36
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gly Gly Trp Thr Leu Asn Ser Ala Gly Tyr Leu Leu Gly Lys Ile Asn
1               5                   10                  15

Leu Lys Ala Leu Ala Ala Leu Ala Lys Lys Ile Leu
            20                  25

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Cys Asp Cys Arg Gly Asp Cys Phe Cys
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Cys Asn Gly Arg Cys
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Cys Pro Arg Glu Cys Glu Ser Ile Cys
1               5

<210> SEQ ID NO 40
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 40

Cys Pro Gly Pro Glu Gly Ala Gly Cys
1               5

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Thr Thr His Trp Gly Phe Thr Leu Cys
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Arg Arg His Trp Gly Phe Glu Phe Cys
1               5                   10

<210> SEQ ID NO 43
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Leu Ser
1

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Cys Gly Arg Arg Ala Gly Gly Ser Cys
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Cys Val Pro Glu Leu Gly His Glu Cys
1               5

```
<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

His Thr Met Tyr Tyr His His Tyr Gln His His Leu
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Val His Ser Pro Asn Lys Lys
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Ser Arg Pro Arg Arg Ser Glu Cys
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Arg Gly Arg Arg Ser Thr
1               5

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ile Cys Arg Arg Ala Arg Gly Asp Asn Pro Asp Asp Arg Cys Thr
1               5                   10                  15

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51
```

-continued

```
Pro Leu Ala Glu Ile Asp Gly Ile Glu Leu Thr Tyr
1               5                  10
```

<210> SEQ ID NO 52
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
His Ser Asp Gly Thr Phe Thr Ser Glu Leu Ser Arg Leu Arg Asp Ser
1               5                  10                  15

Ala Arg Leu Gln Arg Leu Leu Gln Gly Leu Val
            20                  25
```

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Asn Pro Val Val Gly Tyr Ile Gly Glu Arg Pro Gln Tyr Arg Asp Leu
1               5                  10                  15
```

<210> SEQ ID NO 54
<211> LENGTH: 29
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Cys Thr Thr Thr His Thr Phe Val Lys Ala Leu Thr Met Asp Gly Lys
1               5                  10                  15

Gln Ala Ala Trp Arg Phe Ile Arg Ile Asp Thr Ala Cys
            20                  25
```

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Glu Leu Tyr Glu Asn Lys Pro Arg Arg Pro Tyr Ile Leu
1               5                  10
```

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Leu Ser Ile Pro Pro Lys Ala
1               5
```

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Phe Gln Thr Pro Pro Gln Leu
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Thr Pro Ala Thr Ala Ile
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Cys Tyr Ile Gln Asn Cys Pro Leu Gly
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Val Tyr Phe Gln Asn Cys Pro Arg Gly
1               5

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ser Tyr Ser Met Glu His Phe Arg Trp Gly Lys Pro Val
1               5                   10

<210> SEQ ID NO 62
<211> LENGTH: 22
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 62

Ala Glu Lys Lys Asp Glu Gly Pro Tyr Arg Met Glu His Phe Arg Trp
1               5                   10                  15

Gly Ser Pro Pro Lys Asp
            20

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Tyr Val Met Gly His Phe Arg Trp Asp Arg Phe Gly
1               5                   10

<210> SEQ ID NO 64
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Glu Ala Phe Pro Leu Glu Phe
        35

<210> SEQ ID NO 65
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Ser Gln Glu Pro Pro Ile Ser Leu Asp Leu Thr Phe His Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Glu His Trp Ser Tyr Gly Leu Arg Pro Gly
1               5                   10

<210> SEQ ID NO 67
```

```
<211> LENGTH: 3
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu His Pro
1

<210> SEQ ID NO 68
<211> LENGTH: 14
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ala Gly Cys Lys Asn Phe Phe Trp Lys Thr Phe Thr Ser Cys
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Gly Pro Lys Thr Lys Arg Lys Val Gly
1               5                   10

<210> SEQ ID NO 70
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 71
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 72
<211> LENGTH: 28
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 72

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 73
<211> LENGTH: 23
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Phe Asn Ala Pro Phe Asp Val Gly Ile Lys Leu Ser Gly Val Gln Tyr
1               5                   10                  15

Gln Gln His Ser Gln Ala Leu
            20

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Pro Gly Pro Trp Leu Glu Glu Glu Glu Glu Ala Tyr Gly Trp Met Asp
1               5                   10                  15

Phe

<210> SEQ ID NO 75
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

His Ser Asp Gly Thr Phe Thr Ser Glu Leu Ser Arg Leu Asn Asp Ser
1               5                   10                  15

Ala Arg Leu Asn Arg Leu Leu Asn Gly Leu Val
            20                  25

<210> SEQ ID NO 76
<211> LENGTH: 21
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Lys Ala Pro Ser Gly Arg Val Ser Met Ile Lys Asn Leu Gln Ser Leu
1               5                   10                  15

Asp Pro Ser His Arg
            20
```

```
<210> SEQ ID NO 77
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

His Ser Asp Ala Val Phe Thr Asp Asn Tyr Thr Arg Leu Arg Lys Gly
1               5                   10                  15

Met Ala Val Lys Lys Tyr Leu Asn Ser Ile Leu Asn
            20                  25

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Arg Pro Lys Pro Gln Gln Phe Phe Gly Leu Met
1               5                   10

<210> SEQ ID NO 79
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Ala Pro Leu Glu Pro Val Tyr Pro Gly Asp Asn Ala Thr Pro Glu Asn
1               5                   10                  15

Met Ala Gln Tyr Ala Ala Asp Leu Arg Arg Tyr Ile Asn Met Leu Thr
            20                  25                  30

Arg Pro Arg Tyr
            35

<210> SEQ ID NO 80
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Tyr Pro Pro Lys Pro Glu Ser Pro Gly Glu Asp Ala Ser Pro Glu Glu
1               5                   10                  15

Met Asn Lys Tyr Leu Thr Ala Leu Arg His Tyr Ile Asn Leu Val Thr
            20                  25                  30

Arg Gln Arg Tyr
            35

<210> SEQ ID NO 81
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 81

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 82
<211> LENGTH: 29
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Arg Val Tyr Ile His Pro Phe
1               5

<210> SEQ ID NO 84
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Phe Val Pro Tyr Asn Pro Pro Arg Pro Gly Gln Ser Lys Pro Phe Pro
1               5                   10                  15

Ser Phe Pro Gly His Gly Pro Phe Asn Pro Lys Ile Gln Trp Pro Tyr
            20                  25                  30

Pro Leu Pro Asn Pro Gly His
        35

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gly Asn Arg Pro Val Tyr Ile Pro Pro Pro Arg Pro Pro His Pro Arg
1               5                   10                  15

Leu
```

<210> SEQ ID NO 86
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Arg Phe Arg Pro Pro Ile Arg Arg Pro Pro Ile Arg Pro Pro Phe Tyr
1               5                   10                  15

Pro Pro Phe Arg Pro Pro Ile Arg Pro Pro Ile Phe Pro Pro Ile Arg
            20                  25                  30

Pro Pro Phe Arg Pro Pro Leu Gly Pro Phe Pro Gly Arg Arg
        35                  40                  45

<210> SEQ ID NO 87
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Ala Leu Ser Tyr Arg Glu Ala Val Leu Arg Ala Val Asp Arg Ile Asn
1               5                   10                  15

Glu Arg Ser Ser Glu Ala Asn Leu Tyr Arg Leu Leu Glu Leu Asp Pro
            20                  25                  30

Pro Pro Lys Asp Val Glu Asp Arg Gly Ala Arg Lys Pro Thr Ser Phe
        35                  40                  45

Thr Val Lys Glu Thr Val Cys Pro Arg Thr Ser Pro Gln Pro Pro Glu
    50                  55                  60

Gln Cys Asp
65

<210> SEQ ID NO 88
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Lys Phe Thr Ile Val Phe Leu Leu Leu Ala Cys Val Phe Ala Met
1               5                   10                  15

Ala Val Ala Thr Pro Gly Lys Pro Arg Pro Tyr Ser Pro Arg Pro Thr
            20                  25                  30

Ser His Pro Arg Pro Ile Arg Val Arg Arg Glu Ala Leu Ala Ile Glu
        35                  40                  45

Asp His Leu Ala Gln Ala Ala Ile Arg Pro Pro Ile Leu Pro Ala
    50                  55                  60

<210> SEQ ID NO 89
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Ala Phe Pro Pro Pro Asn Val Pro Gly Pro Arg Phe Pro Pro Asn
1               5                   10                  15

Phe Pro Gly Pro Arg Phe Pro Pro Asn Phe Pro Gly Pro Arg Phe
                20                  25                  30

Pro Pro Pro Asn Phe Pro Gly Pro Arg Phe Pro Pro Asn Phe Pro
            35                  40                  45

Gly Pro Pro Phe Pro Pro Pro Ile Phe Pro Gly Pro Trp Phe Pro
        50                  55                  60

Pro Pro Pro Phe Arg Pro Pro Phe Gly Pro Pro Arg Phe Pro
65                  70                  75
```

<210> SEQ ID NO 90
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Cys Tyr Cys Arg Ile Pro Ala Cys Leu Ala Gly Glu Arg Arg Tyr Gly
1               5                   10                  15

Thr Cys Phe Leu Gly Arg Val Trp Ala Phe Cys Cys
                20                  25
```

<210> SEQ ID NO 91
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
                20                  25                  30

Lys Cys Cys Lys
        35
```

<210> SEQ ID NO 92
<211> LENGTH: 18
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Arg Gly Gly Arg Leu Cys Tyr Cys Arg Arg Phe Cys Val Cys Val
1               5                   10                  15

Gly Arg
```

<210> SEQ ID NO 93
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

```
Asp Cys Leu Ser Gly Arg Tyr Lys Gly Pro Cys Ala Val Trp Asp Asn
1               5                  10                 15

Glu Thr Cys Arg Arg Val Cys Lys Glu Glu Gly Arg Ser Ser Gly His
            20                  25                  30

Cys Ser Pro Ser Leu Lys Cys Trp Cys Glu Gly Cys
        35                  40
```

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

```
Asp Glu Asp Met Asp Glu
1               5
```

<210> SEQ ID NO 95
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

```
Ala Leu Trp Lys Thr Met Leu Lys Lys Leu Gly Thr Met Ala Leu His
1               5                  10                 15

Ala Gly Lys Ala Ala Leu Gly Ala Ala Ala Asp Thr Ile Ser Gln Gly
            20                  25                  30

Thr Gln
```

<210> SEQ ID NO 96
<211> LENGTH: 24
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

```
Gly Ile Gly Ala Leu Ser Ala Lys Gly Ala Leu Lys Gly Leu Ala Lys
1               5                  10                 15

Gly Leu Ala Glx His Phe Ala Asn
            20
```

<210> SEQ ID NO 97
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Trp Lys Pro Phe Lys Lys Ile Glu Lys Ala Val Arg Arg Val Arg Asp
1               5                  10                 15

Gly Val Ala Lys Ala Gly Pro Ala Val Ala Val Val Gly Gln Ala Thr
            20                  25                  30
```

<210> SEQ ID NO 98

```
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gly Ile Phe Ser Lys Leu Gly Arg Lys Lys Ile Lys Asn Leu Leu Ile
1               5                   10                  15

Ser Gly Leu Lys Asn Val Gly Lys Glu Val Gly Met Asp Val Val Arg
            20                  25                  30

Thr Gly Ile Asp Ile Ala Gly Cys Lys Ile Lys Gly Glu Cys
        35                  40                  45

<210> SEQ ID NO 99
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Tyr Lys Lys Lys
1

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Tyr Lys Lys Lys Lys Lys Lys Lys
1               5

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Gly Gly Gly Gly Gly
1               5

<210> SEQ ID NO 102
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Lys Lys Lys Lys Lys Lys
1               5

<210> SEQ ID NO 103
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 103

Pro Pro Pro Pro Pro Pro
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Val Arg Lys Lys Arg Lys Thr
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Lys Lys Ser Lys Gln Glu
1               5

<210> SEQ ID NO 106
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Leu Arg Arg
1

<210> SEQ ID NO 107
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Arg Arg Lys
1

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Gly Pro Lys Lys Lys Arg Lys Val Gly
1               5                   10
```